United States Patent [19]

Suzuki et al.

[11] Patent Number: 5,061,481

[45] Date of Patent: Oct. 29, 1991

[54] COSMETIC COMPOSITION HAVING ACRYL-SILICONE GRAFT COPOLYMER

[75] Inventors: Kazuhiro Suzuki; Toru Shimizu; Miki Yamazoe; Tosiaki Sugisaki, all of Tokyo, Japan

[73] Assignee: Kobayashi Kose Co., Ltd., Tokyo, Japan

[21] Appl. No.: 460,629

[22] Filed: Jan. 3, 1990

[30] Foreign Application Priority Data

| Mar. 20, 1989 | [JP] | Japan | 1-68695 |
| Mar. 24, 1989 | [JP] | Japan | 1-72095 |
| Mar. 28, 1989 | [JP] | Japan | 1-76036 |
| Mar. 30, 1989 | [JP] | Japan | 1-79524 |
| Mar. 30, 1989 | [JP] | Japan | 1-79525 |
| Apr. 19, 1989 | [JP] | Japan | 1-99761 |

[51] Int. Cl.$^5$ .............. A61K 7/021; A61K 7/48; A61K 7/06

[52] U.S. Cl. .............. 424/63; 424/61; 424/64; 424/70; 424/78; 514/772; 514/844; 514/845; 514/937; 514/938; 514/944

[58] Field of Search .............. 424/78, 63, 64, 61, 424/70; 514/772, 844, 845, 846, 937, 938, 944

[56] References Cited

U.S. PATENT DOCUMENTS

| 4,136,250 | 1/1979 | Mueller et al. | 528/29 |
| 4,834,972 | 5/1989 | Chang | 428/78 |
| 4,883,852 | 11/1989 | Masuoka et al. | 526/279 |

FOREIGN PATENT DOCUMENTS

| 842947 | 5/1970 | Canada . |
| 199325 | 10/1986 | European Pat. Off. . |
| 2065687 | 7/1981 | United Kingdom . |

OTHER PUBLICATIONS

Patent Abstracts of Japan, vol. 14, No. 176, (C-707)[4119], 9th Apr. 1990, p. 73 C 707; & JP-A-2 25 411, (Kobayashi Kose Co., Ltd.), 26-01-1990.
Patent Abstracts of Japan, vol. 13, No. 595, (C-672)[3943], 27th Dec. 1989, p. 10 C 672; & JP-A-1 250 305, (Kobayashi Kose Co., Ltd.), 05-10-89.
Patent Abstracts of Japan, vol. 13, No. 595, (C-672)[3943], 27th Dec. 1989, p. 10 C 672; & JP-A-1 250 306, (Kobayashi Kose Co., Ltd.), 05-10-1989.

*Primary Examiner*—Thurman K. Page
*Assistant Examiner*—Susan S. Rucker
*Attorney, Agent, or Firm*—Oblon, Spivak, McClelland, Maier & Neustadt

[57] ABSTRACT

Cosmetic comprising (A) a specific acryl-silicone graft copolymer having an organosiloxane side chain is disclosed. The copolymer is prepared by radical polymerization of (i) a dimethylpolysiloxane compound having a polymerizable radical group on one of the molecular chain terminals and (ii) a radically polymerizable monomer comprising as major components an acrylate or methacrylate, or both. Various cosmetics including makeup cosmetics, o/w emulsion cosmetics, and w/o emulsion cosmetics, are prepared by using the copolymer in combination with (B) a low-viscosity silicone oil, (C) a partially cross-linked organopolysiloxane polymeric compound, (D) a low-boiling-point oil, (E) a volatile solvent, (F) a cosmetic powder material, (G) a polyacrylic acid, (H) a volatile hydrocarbon, (I) a surface active agent, or (J) water. The cosmetic compositions give a good sensation upon use, and exhibit superior water-repellency, water-resistance, oil-resistance, and good retentiveness of the makeup.

9 Claims, No Drawings

COSMETIC COMPOSITION HAVING ACRYL-SILICONE GRAFT COPOLYMER

BACKGROUND OF THE INVENTION

1. Field of the Invention

This invention relates to a cosmetic composition, and, more particularly, to a cosmetic composition which comprises a specific acryl-silicone graft copolymer having an organosiloxane side chain, and is useful for various applications to the skin, hair, nails, and the like.

The invention also relates to a gel compopsition which comprises the specific acryl-silicone graft copolymer and a low-viscosity silicone oil.

2. Description of the Background Art

Cosmetics are broadly classified into basic cosmetics such as lotions, creams, emulsions, packs, and the like; makeup cosmetics such as foundations, lipsticks, rouges, eyeliners, mascaras, eyeshadows, eyebrow pencils, manicures, face powders, and the like; and hair cosmetics.

Since basic cosmetics have the purpose of imparting moisturizing and softening effects to the skin, characteristics strongly required for them are good water-retaining capability as well as superior stability and retentiveness of the humectant and softening components. Emulsion cosmetics are widely used as basic cosmetics, makeup cosmetics, and the like, in which the characteristics of emulsion are utilized.

Neither o/w-type nor w/o-type emulsions, however, can provide a composition having sufficient stability over time, good water-repellency, and excellent sensation upon use at the same time.

Since one of the major purposes of makeup cosmetics is to improve the outward appearance of the object to which they are applied, such as the skin and nails, characteristics demanded of makeup cosmetics include a good sensation upon use; superior water-repellency, water-resistance, and oil-resistance; and good retentiveness of the makeup.

Many of conventional makeup cosmetics such as foundations, eyeliners, mascaras, eyeshadows, nail enamels, and so on do not give a good sensation upon use and do not produce a cosmetic film which is sufficiently water-resistant, oil-resistant, and friction-resistant.

In view of this situation, the present inventors have undertaken extensive studies for the development of a cosmetic composition having good stability over time, imparting an excellent sensation upon use, and possessing superior resistance to water and oil. As a result, the present inventors have found that a cosmetic composition and a gel composition into which a specific type of acryl-silicone graft copolymer is incorporated satisfied these requirements for cosmetics.

SUMMARY OF THE INVENTION

Accordingly, an object of this invention is to provide a cosmetic composition comprising an acryl-silicone graft copolymer which is prepared by radical polymerization of (i) a dimethylpolysiloxane compound having a polymerizable radical group on one of the molecular chain terminals and (ii) a radically polymerizable monomer comprising as major components an acrylate or methacrylate, or both [such a graft copolymer is herein referred to as component (A)].

Another object of the present invention is to provide various types of cosmetic compositions in which one or more components selected from the group consisting of a low-viscosity silicone oil [component (B)], a partially cross-linked organopolysiloxane polymeric compound [component (C)], a low-boiling-point oil [component (D)], a volatile solvent [component (E)], a cosmetic powder material [component (F)], a polyacrylic emulsion of the type increasing its viscosity in alkaline conditions, [component (G)], a volatile hydrocarbon [component (H)], a surface active agent [component (I)], and water [component (J)] are used in combination with the above component (A).

Still another object of the present invention is to provide a gel composition which comprises said acryl-silicone graft copolymer and a low-viscosity silicone oil.

Other objects, features and advantages of the invention will hereinafter become more readily apparent from the following description.

DETAILED DESCRIPTION OF THE INVENTION AND PREFERRED EMBODIMENTS

Component (A), the acryl-silicone graft copolymer, of the present invention can be prepared by the radical copolymerization of (i) a dimethylpolysiloxane compound having a polymerizable radical group on one of the molecular chain terminals and (ii) a radically polymerizable monomer comprising as major components an acrylate or methacrylate, or both. The dimethylpolysiloxane compound (i) having a polymerizable radical group on one of the molecular chain terminals is represented by the following general formula (I),

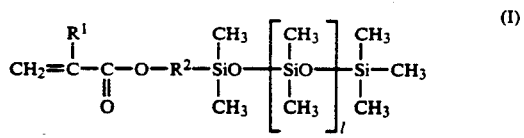

wherein $R^1$ represents a methyl group or a hydrogen atom, $R^2$ represents a divalent, linear or branched hydrocarbon group having 1–10 carbon atoms and optionally containing one or two ether bonds therein, and $l$ is a value of 3–300.

Typical examples of the group represented by $R^2$ include: $-CH_2-$, $-CH_2-_3-$, $-CH_2-_5-$, $-CH_2-_8-$, $-CH_2-_{10}-$, $-CH_2-CH(CH_3)-CH_2-$, $-CH_2CH_2OCH_2CH_2CH_2-$, $-CH_2CH_2OCH_2CH_2CH(CH_3)CH_2-$, $-CH_2CH_2OCH_2CH_2OCH_2CH_2CH_2-$, and the like. The value $l$ is usually 3–300. The preferable range is between 5 and 100. If the value for $l$ is less than 3, the resulting acryl-silicone graft copolymer has a poor mutual solubility with a low-viscosity silicone oil and a low-boiling-point oil and produces a film having only insufficient water-resistance. If the value of $l$ is greater than 300, the resulting acryl-silicone graft copolymer has only a low glass transition temperature. This precludes the copolymer from producing a film having sufficient strength and from producing a solid gel composition having a good quality even though a low-viscosity silicone oil is incorporated.

A process for preparing this dimethylpolysiloxane compound having a polymerizable radical group on one of the molecular chain terminals and represented by the general formula (I) can be exemplified by the de-hydrochloric acid reaction of a (meth)acrylate-substituted chlorosilane compound of the formula (II) and a dimethylpolysiloxane a terminal of which is substituted by a hydroxyl group of the formula (III) according to a conventional method:

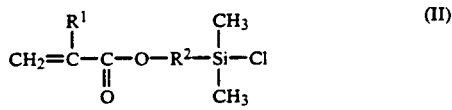

wherein $R^1$ represents a methyl group or a hydrogen atom, $R^2$ represents a divalent, linear or branched hydrocarbon group having 1-10 carbon atoms and optionally containing one or two ether bonds therein,

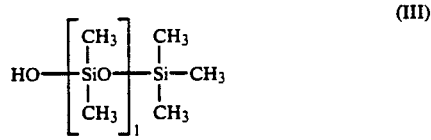

wherein l is a value of 3-300.

The following compounds are give as examples of preferable dimethylpolysiloxane compounds having a polymerizable radical group on one of the molecular chain terminals.

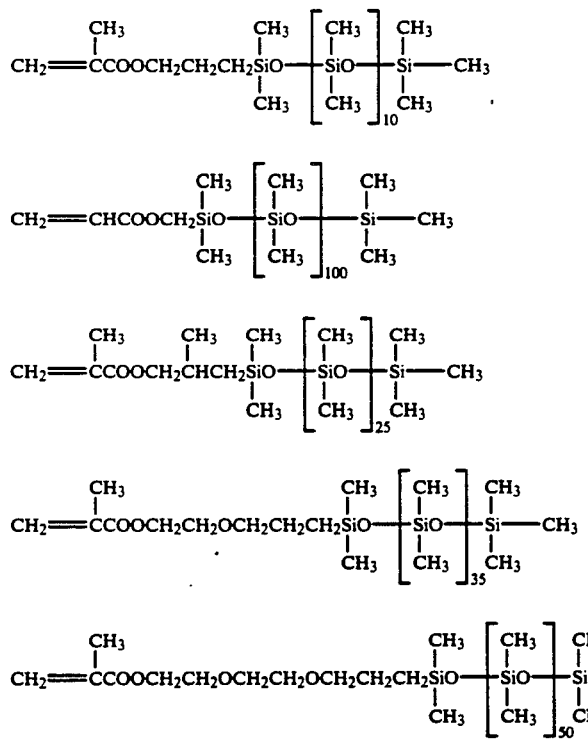

A radically polymerizable monomer (ii) comprising an acrylate or methacrylate, or both as its major components is a compound having one radically polymerizable unsaturated bond in its molecule. Given as examples of acrylates or methacrylates which can be present in the compound are alkyl(meth)acrylates such as methyl(meth)acrylate, ethyl(meth)acrylate, n-butyl(meth)acrylate, 2-ethylhexyl(meth)acrylate, and the like, hydroxyalkyl(meth)acrylates such as 2-hydroxyethyl-(meth)acrylate, 2-hydroxypropyl(meth)acrylate, and the like, and perfluoroalkyl(meth)acrylate having a $C_{1-10}$ fluorocarbon chain. Here, the expression "comprising an acrylate, a methacrylate, or both as major components" means that the radically polymerizable monomer "comprises at least 50% by weight or more of one or more acrylates or methacrylates." If the total amount of acrylates and methacrylates contained in the monomer is less than 50% by weight, the resulting copolymer cannot produce an acceptable film or solid gel composition.

Various other compounds besides acrylates or methacrylates can be used as required for the radically polymerizable monomer of the present invention. Given as examples of such radically polymerizable monomers are styrene, substituted styrenes, vinyl acetate, (meth)acrylic acid, maleic anhydride, maleic acid esters, fumaric acid esters, vinyl chloride, vinylidene chloride, ethylene, propylene, butadiene, acrylonitrile, fluorinated olefins, and the like.

In the present invention, a ratio by weight of (i) a dimethylpolysiloxane compound having a polymerizable radical group on one of the molecular chain terminals and (ii) a radically polymerizable monomer comprising as major components an acrylate or methacrylate, or both, i.e., (i):(ii), in the copolymer should be in the range of 1:19-2:1. If the ratio is less than 1:19, the resulting acryl-silicone graft copolymer has a poor mutual solubility with a low-viscosity silicone oil (B) and a low-boiling-point oil (D) and produces a film having only insufficient water-resistance. If the ratio is more than 2:1, on the other hand, the resulting acryl-silicone graft copolymer cannot produce a film or solid gel composition having high strength.

The copolymerization reaction of (i) a dimethylpolysiloxane compound having a polymerizable radical group on one of the molecular chain terminals and (ii) a radically polymerizable monomer comprising as major components an acrylate or methacrylate, or both can be carried out using a conventional radical polymerization initiator such as benzoylperoxide, lauroylperoxide, azobisisobutyronitrile, or the like. Solution polymerization, emulsion polymerization, suspension polymerization, and bulk polymerization can be acceptable. Among these, solution polymerization is preferable because of its capability of readily adjusting the molecular weight of the resulting graft copolymer to an optimum range. A solvent which can be used in the reaction is an aromatic hydrocarbon such as benzene, toluene, xylene, or the like; a ketone such as methyl ethyl ketone, methyl isobutyl ketone, or the like; an ester such as ethyl acetate, isobutyl acetate, or the like; or an alcohol such as isopropanol, butanol, or the like. Such solvents may be used independently or two or more types of solvents may be used in a mixture.

The polymerization reaction is carried out at a temperature range of 50°–180° C., preferably of 60°–120° C. The reaction is usually completed in 5–10 hours under these conditions. The acryl-silicone graft copolymer thus produced has a weight average molecular weight of about 3,000–200,000, preferably of about 5,000–100,000, converted to polystyrene by gel permeation chromatography analysis. A preferable range of the glass transition temperature of the copolymer is between −30° and +60° C.

A stable gel composition can be produced by incorporating a low-viscosity silicone oil (B) into the copolymer (A). The gel composition is solid, soft, and stable, and gives a smooth and fresh sensation upon use.

There are no specific limitations as to the type of a low-viscosity silicone oil for use. Any silicone oils having a viscosity below 50 cs, preferably of 2–20 cs, can suitably be used. The use of a large amount of a higher viscosity silicone oil may decrease the mutual solubility of the silicone oil and copolymer (A). This results in an oily sensation and tends to impair the feeling upon use of the resulting product. Examples of low-viscosity silicone oils include low-polymerization-degree dimethylpolysiloxanes, methylphenylpolysiloxane, and the like. If necessary, two or more of low-viscosity silicone oils can be used in combination.

The gel composition of the present invention can be prepared by blending component (A) and a low-viscosity silicone oil (B) and heating the mixture to dissolution, or by dissolving component (A) into a volatile organic solvent and adding a low-viscosity silicone oil (B) to the solution, followed by removal of the volatile organic solvent. The ratio of component (A) and a low-viscosity silicone oil (B) varies depending on the types of component (A). Normally, the ratio by weight of (A):(B) is 5:95–70:30, with a preferable range being 15:85–40:60. If the amount of the low-viscosity silicone oil (B) is too large in proportion to copolymer (A), the resulting gel composition becomes fluid so that a gel composition having acceptable solidity cannot be obtained. If the amount of copolymer (A) is too large, on the other hand, a soft, flexible solid gel composition cannot be obtained.

In the present invention, a solid gel composition having varied solidity, ranging from a comparatively hard gel to a comparatively soft gel, can be produced by changing the proportion of component (A) and a low-viscosity silicone oil (B), or the acryl chain length, silicone chain length, or the amount of the substitution in the copolymer. If the proportion of the copolymer (A) is increased or a larger amount of methylmethacrylate is introduced into the acryl chains of the copolymer, a solid gel giving suitable solidity to touch is obtained. On the other hand, a soft, flexible gel composition can be produced by introducing a large amount of butylacrylate or 2-ethylhexylacrylate into the acryl chains of the copolymer.

The solid gel composition thus prepared gives a soft, stable, smooth, and fresh sensation upon use. By using the solid gel composition as a component, very useful cosmetic compositions, in which the excellent characteristics of the solid gel are fully exhibited, can be produced. Such cosmetics include basic cosmetics for use with the face, hands, and feet such as creams, emulsions, and the like; hair cosmetics such as hair treatment agents and the like; and makeup cosmetics such as foundations, rouges, face powders, lipsticks, eyeliners, eyeshadows, mascaras, and the like. The kinds of cosmetics to which the gel composition of the present invention is applied are by no means limited to those given here.

The amount of the solid gel to be incorporated into a cosmetic composition can be determined depending on the use to which the cosmetic composition is directed within a range of 1–100% by weight. The use of the solid gel alone may achieve the purpose of the present invention.

A gel composition comprising: (A) 5–60% by weight of an acryl-silicone graft copolymer, (B) 30–94.8% by weight of a low-viscosity silicone oil, and (C) 0.2–40% by weight of a partially cross-linked organopolysiloxane polymeric compound is particularly useful for incorporating in a cosmetic composition. When such a gel composition is incorporated in an amount of 30–100% by weight, the cosmetic composition gives a smooth and fresh feeling upon use, is easy to use, and exhibits excellent stability over time.

The amount of 5–60% by weight of an acryl-silicone graft copolymer is preferable, this is because the intended effect cannot be produced if the amount is less than 5% by weight and the cosmetic composition becomes too hard at an amount exceeding 60% by weight such that the solid cosmetic composition cannot readily be applied. In addition, a solid cosmetic composition of this type gives the feeling of a thick membrane after application.

Silicone oils of the type mentioned above can be used as a low-viscosity silicone oil (B) either independently or in combination. A desirable range to be incorporated is 30–94.8% by weight.

A partially cross-linked organopolysiloxane polymeric compound (C) used in the cosmetic composition of the present invention is that having a cross-linking three-dimensional structure, encompassing a low-viscosity silicone oil, and capable of forming a gel.

The partially cross-linked organopolysiloxane polymeric compound which can be used may include, for example, an organopolysiloxane polymeric compound which is insoluble in benzene and has a three-dimensional cross-linked structure in which benzene of an equivalent or more amount of the organopolysiloxane polymeric compound itself may be contained. Such a polymeric compound can be prepared by the cross-linking reaction of organopolysiloxane, may contain three-dimensional cross-linking structures, and consists of $R_2SiO$ and $RSiO_{1.5}$ units. The polymeric compound may also contain $R_3SiO_{0.5}$, $SiO_2$, or both.

Given as examples of R in the above organopolysiloxane constituting unit are the hydrogen atom, an alkyl group such as methyl, ethyl, propyl, or the like, an aryl group such as phenyl, tolyl, or the like, and an unsaturated aliphatic group such as vinyl group. The organosiloxane unit may contain either one type of R, or two or more different types of R.

In order for the organopolysiloxane to be insoluble in benzene and to take a three-dimensional cross-linked structure in which benzene of an equivalent or more amount of the organopolysiloxane polymeric compound itself may be contained, it is essential that the ratio of either $RSiO_{1.5}$, $SiO_2$, or $RSiO_{1.5}$ plus $SiO_2$, and either $R_2SiO$, $R_3SiO_{0.5}$, or $R_2SiO$ plus $R_3SiO_{0.5}$, be in a suitable range. If the amount of either $RSiO_{1.5}$, $SiO_2$, or $RSiO_{1.5}$ plus $SiO_2$, is too small in proportion to the amount of either $R_2SiO$, $R_3SiO_{0.5}$, or $R_2SiO$ plus $R_3SiO_{0.5}$, the organopolysiloxane does not take a sufficient degree of three-dimensional cross-linked structure and is soluble in benzene. This type of organopolysiloxane cannot be used for the purpose of this invention, even though it may contain a cross-linked structure. On the other hand, if the amount of either $RSiO_{1.5}$, $SiO_2$, or $RSiO_{1.5}$ plus $SiO_2$, is too large in proportion to the amount of either $R_2SiO$, $R_3SiO_{0.5}$, or $R_2SiO$ plus $R_3SiO_{0.5}$, the cross-linked structure of organopolysiloxane becomes so hard that it only contains benzene in an amount less than the amount of organopolysiloxane itself, even though it is insoluble in benzene. This type of organopolysiloxane cannot be used for the purpose of this invention, since it separates and is released from an organopolysiloxane-low-viscosity silicone oil mixture.

The ratio of the $R_2SiO$ unit to the $RSiO_{1.5}$ unit in an organopolysiloxane polymeric compound which is insoluble in benzene and may contain an equivalent or more amount of benzene cannot be strictly specified because of significant involvement of the molecular weight magnitude of the whole organopolysiloxane polymeric compound, as another factor. In practice, however, a ratio of 1:1 to 30:1 gave good results. If the amount of the $RSiO_{1.5}$ unit is in a higher side above this ratio, the organopolysiloxane polymeric compound becomes too hard to contain the equivalent amount of benzene in it. This type of organopolysiloxane does not sufficiently swell when it is mixed with a low-viscosity silicone oil. Silicone oil separates and is released from the mixture. This impairs the stability of the composition. On the other hand, if the amount of the $R_2SiO$ unit is in a higher side above the above-mentioned ratio, the structural viscosity properties of the organopolysiloxane is lessened. Because of these reasons, the above-mentioned range of the organopolysiloxane structural unit ratio is desirable in order to produce a superior silicone gel composition which is both soft and stable.

An organopolysiloxane polymeric compound, insoluble in benzene and having a three-dimensional cross-linked structure which may contain benzene in an equivalent or more amount of the weight of itself, can be prepared by various methods. Examples of such methods include:

(1) A dehydrogenation-condensation reaction of an organohydrogenpolysiloxane having at least 2 hydrogen atoms which are combined with a silicon atom in a molecule. The dehydrogenation-condensation reaction is carried out in the presence of a catalytic amount of an alcoholic aqueous solution of an alkali metal hydroxide and under heating.

(2) A dehydrogenation-condensation reaction of an organohydrogenpolysiloxane having at least 2 hydrogen atoms which are combined with a silicon atom in one molecule and an organopolysiloxane having at least 2 hydroxyl groups which are combined with a silicon atom in one molecule. This dehydrogenation-condensation reaction is carried out in the presence of a catalytic amount of an alkali metal hydroxide or a platinum compound and under heating.

(3) A dehydration-condensation reaction of an organopolysiloxane having at least 2 hydroxyl groups which are combined with a silicon atom in a molecule. The dehydration-condensation reaction is carried out in the presence of a catalytic amount of an alkali metal hydroxide or an organo-tin compound and under heating (4) A dealcohol reaction of an organopolysiloxane having at least 2 hydroxyl groups which are combined with a silicon atom in one molecule and another organopolysiloxane having at least 2 alkoxy groups which are combined with a silicon atom in one molecule. The dealcohol reaction is carried out in the presence of a catalytic amount of an alkali metal hydroxide or an organo-tin compound and under heating.

All of these methods can easily produce an organopolysiloxane polymeric compound which is insoluble in benzene and has a three-dimensional cross-linked structure capable of containing benzene of an equivalent or more amount of the organopolysiloxane polymeric compound itself.

As another example of a partially cross-linked organopolysiloxane polymeric compound (C), an organopolysiloxane polymeric compound which is insoluble but sufficiently swells in silicone oil is given. This organopolysiloxane polymeric compound is prepared by the addition polymerization of (iii) an organohydrogenpolysiloxane and (iv) an organopolysiloxane having unsaturated aliphatic groups, and contains a partial three-dimensional cross-linked structure.

The organohydrogenpolysiloxane (iii) used in the addition polymerization is comprised of units $HSiO_{1.5}$, $RSiO_{1.5}$, $RHSiO$, $R_2SiO$, $R_2HSiO_{0.5}$, $R_3SiO_{0.5}$, and the like. This compound may take either a linear, branched, or cyclic molecular structure, and contains at least 2 hydrogen atoms which are combined with a silicon atom in a molecule. For better control of the reaction producing the organopolysiloxane polymeric compound, the organohydrogenpolysiloxane used should have a linear structure. The hydrogen atom bonded to the silicon atom, i.e., H in —SiH bond, of the organohydrogenpolysiloxane molecule is usually contained within the molecular chain. It may, however, be at the molecular chain terminals. A preferable amount of the —SiH bond is usually 1–20 mol% when the molecular structure is linear or branched, and 1–50 mol% when the molecular structure is cyclic. A preferable organohydrogenpolysiloxane is that containing 50 mol% or more of a methyl group of organic groups other than —SiH bond.

The above-mentioned organopolysiloxane (iv) having unsaturated aliphatic groups which is used in the addition polymerization reaction is that containing at least 2 unsaturated aliphatic groups which are bonded to a silicon atom in a molecule. Given as examples of this type of organopolysiloxane are those containing a vinyl group or an allyl group. Usually, an organovinylpolysiloxane containing a vinyl group is used. A specific example of organovinylpoly-siloxane is that containing units $(CH_2=CH)SiO_{1.5}$, $RSiO_{1.5}$, $R(CH=CH_2)SiO$, $R_2SiO$, $R_2(CH=CH_2)SiO_{0.5}$, $R_3SiO_{0.5}$, and the like. The molecular structure may be either linear, branched, or cyclic, and one which contains at least 2 unsaturated aliphatic groups, e.g. a vinyl group, in one molecule.

For better control of the reaction of producing the organopolysiloxane polymeric compound, an organopolysiloxane having unsaturated aliphatic groups used should have a linear structure. This type of organovinylpolysiloxane usually has a linear structure having dimethylvinylsilyl groups at its both ends of the molecule. The vinyl group, however, must be within the molecular chain. A preferable amount of the vinyl group is usually 1-20 mol% when the molecular structure is linear or branched, and 1-50 mol% when the molecular structure is cyclic. A preferable organovinylpolysiloxane is that containing 50 mol% or more methyl group of organic groups other than a vinyl group.

It is essential for the organohydrogenpolysiloxane (iii) and organopolysiloxane having unsaturated aliphatic groups (iv), e.g. organovinylpolysiloxane, to produce an addition polymerization compound having a three-dimensional structure in part of which these organopolysiloxanes (iii) and (iv) contain at least 2 reactive groups, i.e., hydrogen atoms, bonded to a silicon atom or a vinyl group. If the amount of these reactive groups contained in organopolysiloxanes (iii) or (iv) is greater than 20 mol%, in the case where organopolysiloxanes have linear or branched structures, or is greater than 50 mol%, in the case where organopolysiloxanes have a cyclic structure, the polymers produced become stiff. In addition, a low-viscosity silicone oil tends to be encompassed by the three-dimensional structure of such polymers only with difficulty, and to separate and be released from the mixture, thus resulting in a less stable product. Conversely, if the content of the reactive groups is less than 1%, the structural viscosity properties of the organopolysiloxane tends to be lessened. Because of these reasons, although not restrictive, the amount of the reactive groups contained in organopolysiloxanes (iii) or (iv) is 1-20 mol%, in the case where organopolysiloxanes have linear or branched structures, or 1-50 mol%, in the case where organopolysiloxanes have a cyclic structure, in order to produce a superior silicone gel composition which is both soft and stable.

Given as examples of the organic group R in the constituting unit of the above organohydrogenpolysiloxane (iii) are an alkyl group such as methyl, ethyl, propyl, butyl, or the like, an aryl group such as phenyl, tolyl, or the like, or cyclohexyl group. R may also be a substituted mono-valent hydrocarbon group, other than unsaturated aliphatic hydrocarbon groups such as a vinyl group. The substitution group may be a halogen atom, cyano group or the like.

A typical example of such an organohydrogenpolysiloxane is a methylhydrogenpolysiloxane containing units $(CH_3)_3SiO-$, $-[(CH_3)_2SiO]_p-$, $-[(CH_3)HSiO]_q-$, and $-Si(CH_3)_3$, wherein p is a value of 10-500 and q is a value of 2-50.

The organic group R contained in organovinylpolysiloxane, which is an organopolysiloxane having unsaturated aliphatic groups (iv), has the same meaning as the R for organohydrogenpolysiloxanes. A typical example of such an organovinylpolysiloxane is that containing units $(CH_2=CH)(CH_3)_2SiO-$, $-[(CH_3)_2SiO]_r-$, and $-Si(CH_3)_2(CH=CH_2)$, wherein r is a value of 10-100, or that containing units $(CH_3)_3SiO-$, $-[(CH_3)_2SiO]_m-$, $-[(CH=CH_2)(CH_3)SiO]_n-$, and $-Si(CH_3)_3$, wherein m is a value of 10-500 and n is a value of 2-50. These organovinylpolysiloxanes are suitable materials and may be used either individually or as a mixture.

The addition polymerization reaction of the organohydrogenpolysiloxane (iii) and organopolysiloxane having unsaturated aliphatic groups (iv) can be carried out according to a commonly known method For example, a target organopolysiloxane polymeric compound which is insoluble in a silicone oil can be easily prepared by reacting an organohydrogenpolysiloxane and an organovinylpolysiloxane, at a proportion such that the molar ratio of the $\equiv$SiH group and vinyl group is in the range of 1:3-3:1, under heating while stirring in the presence of a platinum or palladium addition polymerization catalyst. An especially preferable addition polymerization catalyst is chloroplatinic acid described in Japanese Patent Publication No. 9969/1958.

It is desirable that the partially cross-linked organopolysiloxane polymeric compound (C) be incorporated in an amount of 0.2-40% by weight of the gel composition. The intended effect cannot be obtained if the amount is less than 0.2% by weight If the amount exceeds 40% by weight, on the other hand, the gel composition becomes too soft to maintain a solid state. This also applies to the cosmetic composition to which the gel is incorporated.

Such a gel composition can be prepared by simply blending the acryl-silicone graft copolymer, the low-viscosity silicone oil, and the partially cross-linked organopolysiloxane polymeric compound. An alternative method is to prepare a gel composition from the acryl-silicone graft copolymer and the low-viscosity silicone oil, and a gel composition from the partially cross-linked organopolysiloxane polymeric compound and the low-viscosity silicone oil, followed by blending the two gel compositions. This latter method can produce a gel composition having different characteristics from that produced by blending the three components at the same time. Specifically, such a gel composition can contain a greater amount of silicone oil in a more stable manner. This provides the resulting cosmetic composition with superior smoothness and freshness as well as even better stability over time.

The gel composition which has been fully discussed above is incorporated in an amount of 30-100% by weight based on the total weight of the cosmetic composition.

The cosmetic composition of the present invention can be used as makeup cosmetics such as eyeshadows, foundations, face powders, rouges, lipsticks, eyeliners, mascaras, and the like, hair cosmetics, as well as basic cosmetics such as eyestick and the like.

Among the above essential components, the acryl-silicone graft copolymer (A) has an excellent film-forming capability. Thus, the cosmetic composition to which this component is incorporated can produce a film exhibiting a superior water-resistance, oil-resistance, and other characteristics required for cosmetic films. Taking a cosmetic composition for application to nails such as a nail enamel as an example, such a cosmetic composition can be prepared by dissolving the copolymer (A) into a low-boiling-point oil (D) or a volatile solvent (E). The cosmetic composition thus prepared can produce a continuous film immediately upon application. The low-boiling-point oil (D) used here includes volatile hydrocarbon oils having a boiling point below 260° C. at normal pressure. There are no special limitations as to the types of hydrocarbons. Any types usually used for cosmetics can be used. Specific examples include IP Solvent (trademark; manufactured by Idemitsu Petrochemical Co., Ltd.), Shellsol (trademark; manufactured by Shell Chemical Co., Ltd.), Isoper (trade mark; manufactured by Esso Chemical Co.), and the like. Another type of low-boiling-point oil (D) is a volatile, linear or cyclic silicone oil having a boiling point below 260° C. at normal pressure and a viscosity below 2 cs, such as dimethylpolysiloxane of a low polymerization degree, octamethylcyclotetrasiloxane, decamethylcyclopentasiloxane, and the like. Examples of a volatile solvent (E) include ethyl acetate, butyl acetate, acetone, toluene, and the like. The amount of copolymer (A) to be incorporated into the cosmetic composition is usually 10–70% by weight, and preferably 30–60% by weight. The film produced by the cosmetic composition becomes so thin that the intended effect cannot be exhibited if the amount of copolymer (A) is too small. Too much inclusion of the copolymer (A), on the other hand, results in a high-viscosity product which is hard to apply to nails. Characteristics of films produced by conventional cosmetics are controlled by the addition of camphor, phthalic acid derivative, or alkyd resin. In the cosmetic composition of the present invention, however, such characteristics can be controlled by adjusting the acrylic chain composition or silicone chain length distribution in the copolymer (A). For example, a hard film can be produced by introducing a large amount of methylmethacrylate into acrylic chains, while a soft film that is more soluble in a solvent can be produced by using a greater amount of butylacrylate or 2-ethyl-hexylacrylate. A smooth, slippery film is obtained when a long-chain silicone is used.

A non-aqueous-type makeup cosmetic such as eyeliner, mascara, or the like can be produced by dissolving the copolymer (A) into the aforementioned volatile hydrocarbon oil or volatile silicone oil. The volatile component evaporates when this type of makeup cosmetic is applied to the object, thereby producing a continuous film. The amount of copolymer (A) to be incorporated into such a makeup cosmetic composition is usually 5–60% by weight, and preferably 10–40% by weight. Since a continuous film cannot be produced, the intended effect cannot be adequately exhibited if the amount of copolymer (A) is too small, although this will depend on other components such as waxes or pigments. If the amount of the copolymer (A) is too large, the viscosity becomes so high that the usability of the product is impaired. In addition the film gets so hard that it is difficult to remove it using a removing agent. When the product is an eyeliner, the removing operation will damage the area around the eye.

Another makeup cosmetic composition produced from the acryl-silicone graft copolymer (A) of the present invention is that comprising, in addition to the copolymer (A), a low-boiling-point oil (D), a cosmetic powder material (F), and a polyacrylic emulsion of the type increasing its viscosity under alkaline conditions (G). Such a makeup cosmetic composition produces a uniform film which possesses improved water-resistance, oil-resistance, and adhesiveness. It gives a good sensation upon use and exhibits a prolonged makeup effect. Superior stability over time can be achieved without necessarily using an emulsifier.

It is desirable that the copolymer (A) be incorporated into the makeup cosmetic composition of the present invention in an amount of 5–20% by weight. The effect of the present invention cannot be obtained if the amount is smaller than 5 % by weight. If the amount exceeds 20% by weight, the resulting makeup cosmetic composition has a high viscosity. This makes it uneasy to apply the makeup cosmetic composition and produces a thick-film sensation after the application.

The aforementioned volatile hydrocarbons or silicone oils having a boiling point below 260° C. at normal pressure can be used as the low-boiling-point oil (D). They can be used either independently or as a mixture. Their amount in the makeup cosmetic composition is 5–30% by weight, and preferably 7–20% by weight. The low-boiling-point oil (D) functions as a solvent of the copolymer (A). It also plays a very important role in promoting the life of the cosmetic film.

There are no specific limitations as to the cosmetic powder material (F) used in the makeup cosmetic composition. It may be a body pigment, inorganic white pigment, inorganic colored pigment, organic pigment, organic powder, pearling agent, or the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine blue, tar pigment, nylon powder, polyethylene powder, methylacrylate powder, polystyrene powder, polytetrafluoroethylene powder, silk powder, crystalline cellulose, starch, titanated mica, iron oxide titanated mica, bismuth oxychloride, and the like. These cosmetic powders may be used after a surface-treatment with an oily agent such as silicone or the like. They can be used independently, or two or more of them can be used in combination.

The amount of the cosmetic powder material used for the makeup cosmetic composition can be determined depending on the intended use or purpose without limitation. Usually, an amount of 5–40% by weight is preferable.

Examples given as a polyacrylic emulsion of the type increasing its viscosity under alkaline conditions, which is the component (G), are homopolymers of acrylic acid or methacrylic acid, their copolymers, and partially cross-linked acrylic acid polymers. They increase their viscosities when neutralized with an alkali. These component (G) emulsions may be used independently, or two or more of them can be used in combination. The amount of the component (G) to be incorporated in the cosmetic composition of the present invention is 1–10% by weight. Within this range, the component (G) can homogeneously disperse the solution of the acryl-silicone graft copolymer (A) in the low-boiling-point oil (D) in an aqueous phase. If the amount is less than 1% by weight, the dispersion can be achieved only insufficiently, resulting a product having an inadequate viscosity. If the amount is greater than 10% by weight, on the other hand, the product becomes too viscous to be conveniently applied. Any alkaline substance commonly used for cosmetics can be used to neutralize the polyacrylic emulsion and to raise its viscosity. Given as examples of alkalis which can be suitably used are inorganic alkalis such as sodium hydroxide and potassium hydroxide, basic amino acids such as L-arginine, amines such as triethanolamine, and ammonia, and the like. The amount of alkali used in the cosmetic composition is determined taking into account the type of the alkali and the type of polyacrylic emulsion which are used for preparing the cosmetic composition. Usually, a preferable amount is 0.03–2.5% by weight. The alkali is added, for example, by dissolving it in water in advance, or by directly mixing it with the polyacrylic emulsion. The method of the addition of an alkali, however, is not limited by these.

Furthermore, an o/w-type emulsion cosmetic composition can be prepared by using the copolymer (A) and the low-boiling-point oil (D) at a specific proportion. This o/w-type emulsion cosmetic composition exhibits a smooth spreadability on the skin without imparting an oily sensation, and yet, upon application, produces a film having excellent water-repellency It also possesses good stability over time.

This o/w-type emulsion cosmetic composition comprises 10–40% by weight of an oily component mixture which comprises 2–40% by weight of the copolymer (A) and 20–60% by weight of the low-boiling-point oil (D), wherein the amount of components (A) plus (D) in the total oily component mixture is 60–100% by weight. The copolymer (A) plays an important role in the high water-repellency possessed by the o/w-type emulsion cosmetic composition. The amount of this copolymer in the oily component mixture is in the range of 2–40% by weight. An amount of less than 2% by weight does not produce a sufficient water-repelling characteristic in the emulsion cosmetic composition. An amount exceeding 40% by weight of the copolymer in the mixture raises the viscosity of the resulting emulsion cosmetic composition. This affects the readiness in the application of the emulsion cosmetic composition to the skin and imparts an oily feeling to the skin. The aforementioned low-boiling-point oils can be used as the component (D) for the oily component mixture for producing an o/w-type emulsion cosmetic composition. They may be used independently or two or more of them can be used in combination. The low-boiling-point oil (D) dissolves the copolymer (A) thereby producing a homogeneous oil phase. After application of the emulsion cosmetic composition, it evaporates leaving a good cosmetic film on the skin. This is because in the course of evaporation of the component (D) the crystalline structure of the acrylic portion of the copolymer (A) is enhanced, which improves the characteristics of the film produced. The amount of the low-boiling-point oil in the oil component mixture is suitably determined taking into account the amount of copolymer (A) and other factors Usually, the preferable amount is 20–60% by weight. If the amount is smaller than 20 % by weight, the resulting cosmetic composition in which a comparatively large amount of the copolymer (A) is incorporated exhibits only poor spreadability and imparts an oily feeling upon use. If greater than 60% by weight, a longer time is required for the emulsion cosmetic composition to be fixed and the cosmetic composition tends to leave a thin film after makingup. The total amount of the copolymer (A) and the low-boiling-point oil (D) in the oil component mixture is 60–100% by weight, and preferably 60–98% by weight. If the amount is smaller than 60% by weight, the water-repellency and the excellent feeling upon use of the resulting emulsion cosmetic composition are lost.

Oil components other than the copolymer (A) and the low-boiling-point oil (D) which can be used for the oil component mixture for producing the emulsion cosmetic composition of the present invention may be liquid, semisolid, or solid oils. Specific examples include liquid, pasty, or solid hydrocarbons such as liquid paraffin, squalane, and the like; waxes, higher fatty acids, higher alcohol, esters, glycerides, silicone oils, and the like. These oil components may be used independently or two or more of them can be used in combination. They form a homogeneous oil phase together with the copolymer (A) and low-boiling-point oil (D). They also function as a plasticizer in the formation of a resin by the copolymer (A) when the low-boiling-point oil (D) evaporates. The oil component mixture containing a low-viscosity silicone oil is particularly preferable. The stability of the cosmetic composition and the feeling upon use can be remarkably promoted by the use of such a component mixture.

The oil component mixture comprising the above components is used in the o/w-type emulsion cosmetic composition of the present invention in an amount of 10–40% by weight. If the amount is smaller than 10% by weight, a sufficient water-repelling effect cannot be obtained. On the other hand, if the amount is greater than 40% by weight, the stability of the emulsion cosmetic composition tends to be impaired.

The o/w-type emulsion cosmetic composition can be prepared by emulsifying the oil phase and the water phase according to a conventional method. It can be made into a cream, lotion, or the like.

A makeup cosmetic composition comprising the acryl-silicone graft copolymer (A), a low-viscosity silicone oil (B) and/or a low-boiling-point oil (D), and a cosmetic powder material (F) is an another embodiment of the present invention. This makeup cosmetic composition has excellent water-repellency, oil-resistance, and water-resistance. It gives a good feeling upon use, and its makeup effect lasts for a long period.

It can easily be prepared by using components (A), (B), (D), and (F) which are already described above.

Among this type of makeup cosmetic composition, a non-aqueous-type makeup cosmetic composition comprising 5.0–30.0% by weight of the acryl-silicone graft copolymer (A), 2.5–30.0% by weight of the low-viscosity silicone oil (B), 20.0–80.0% by weight of a volatile hydrocarbon (H), and 10.0–50.0% by weight of a cosmetic powder material (F) is an outstanding feature. It has excellent stability and water or sweat resistance, gives a good feeling upon use, and yet possesses even improved oil or sebum resistance, and friction resistance.

The acryl-silicone graft copolymer (A) is incorporated into the cosmetic composition in an amount of 5.0–30.0% by weight. If less than 5.0% by weight, the intended effect cannot be obtained. If greater than 30.0% by weight, the cosmetic film produced gives a thick feeling.

The aforementioned low-viscosity silicone oil can be used as the component (B) in an amount of 2.5–30.0% by weight. The intended effect cannot be obtained resulting in a film with insufficient softness if the amount of component (B) is less than 2.5% by weight. With the amount exceeding 30.0% by weight, on the other hand, it takes a long period of time for the makeup to fix after the application. The cosmetic film produced is so thin that the makeup gives only an unsatisfactory feeling to the user.

The volatile hydrocarbon (H) of the type previously mentioned is used. This component maintains the copolymer (A) in an well-dissolved condition in the cosmetic composition evaporates after the cosmetic composition is applied to the skin, thus ensuring the formation of a good cosmetic film. That is to say, in the course of evaporation the crystalline structure of the acrylic portion of the copolymer (A) is enhanced, thus producing a firm film which last over a long period of time. It is desirable that the volatile hydrocarbon (H) be incorporated in an amount of 20.0–80.0% by weight. If the amount is smaller than 20.0% by weight, the cosmetic composition produced has a higher viscosity and does not spread well over the skin when applied. This leads to difficulty in forming a homogeneous film.

It is desirable that the cosmetic powder material (F) be added in an amount of 10.0-50.0% by weight of the total amount of the cosmetic composition. The specific amount depends on the intended use and intended application of the cosmetic composition.

The non-aqueous-type makeup cosmetic composition of the present invention can be prepared by blending the above components according to a conventional method and can be prepared into various forms, including a liquid in which the cosmetic powder materials are homogeneously dispersed or precipitated, and a cream. The cosmetic composition is applied to foundations, eyeshadows, rouges, face powders, and the like.

As still another embodiment, the present invention provides a w/o-type emulsion cosmetic composition comprising 0.3-30% by weight of an acryl-silicone graft copolymer (A), 15-57% by weight of a low-viscosity silicone oil (B) and/or a low-boiling-point oil (D), 0.1-10% by weight of a surface active agent (I), and 5-69.9% by weight of water (J). In this composition the total amount of (a) component (A) plus (b) component (B) and/or (D) is 30-60% by weight. This w/o-type emulsion cosmetic composition has good stability over time, produces a film exhibiting a superior water-repellency, and gives an excellent feeling upon use. One or more types of the copolymers (A) can be used and incorporated into the w/o-type emulsion cosmetic composition in an amount of 0.3-30% by weight. An amount smaller than 0.3% by weight does not give the sufficient intended effect. If the amount of the copolymer (A) exceeds 30% by weight, the resulting cosmetic composition gives a heavy feeling to the skin when applied. In addition, an oily feeling impairs the use value of the product.

The above-mentioned low-viscosity silicone oil (B) and low-boiling-point oil (D) can be used in this w/o-type emulsion cosmetic composition. The total amount of the components (B) and (D) is 15-57% by weight of the cosmetic composition. If the amount is less than 15% by weight, and especially the amount of the low-viscosity silicone oil is too small, a smooth, water-repellent characteristic cannot effectively be exhibited.

Besides the above essential oil components (A), (B) and (D), synthetic or natural cosmetic oils conventionally used for cosmetics can be incorporated to the extent that the homogeneity of the oil phase is not adversely affected.

The copolymer (A) and the low-viscosity silicone oil (B) and/or the low-boiling-point oil (D) are incorporated into the w/o-type emulsion cosmetic composition in an amount of 30-60% by weight in total. An amount less than 30% by weight of these oil components gives the intended effect.

Any oxyalkylene-modified organopolysiloxane type surface active agents which can emulsify water into the oil components (A) and (B) and/or (D) can be used as the component (I) without special restriction. Oxyalkylene-modified organopolysiloxanes include polyether-modified silicones and alkyl-polyether-modified silicones. Organopolysiloxanes shown be the following formulae (IV) or (V) are given as examples.

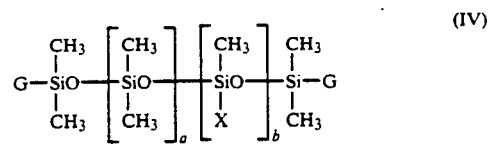

wherein G represents $CH_3$ or $(CH_2)_p(C_2H_4O)_m(C_3H_6)_nR_1$, wherein p is 1-5, m is 1-50, and n is 0-30; $R_1$ represents a hydrogen atom or an alkyl group having 1-5 carbon atoms; X represents $(CH_2)_p(C_2H_4O)_m(C_3H_6)_nR_1$, wherein p, m, and n have the same meanings as defined above; a is a value of 5-300; and b is a value of 1-50.

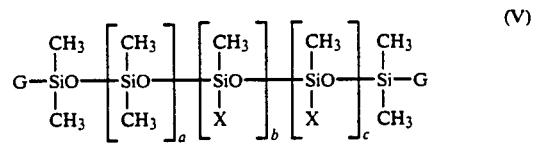

wherein G and X have the same meanings as defined for formula (IV), a is a value of 1-30; and b is a value of 1-50, c is a value of 5-300, and $R_2$ represents an alkyl group having 2-20 carbon atoms.

Among these, those that are liquid or paste at normal temperature and water-insoluble are preferable. Specific examples are Silicone KF-945 (trade mark, Shin-etsu Chemical Co., Ltd.), Silicone SH-3772C (trade mark, Toray Silicone Co., Ltd.), and the like. Since such an oxyalkylene-modified organopolysiloxane has a polysiloxane as the main chain, its mutual solubility with the acryl-silicone graft copolymer (A), low-viscosity silicone oil (B) and low-boiling-point oil (D) is excellent. This contributes to the formation of a stable emulsion.

An amount of 0.1-10% by weight, preferably of 0.5-5% by weight, of the surface active agents (I) is incorporated into the w/o-type emulsion cosmetic composition. If the amount is less than 0.1% by weight, a sufficient emulsification effect cannot be exhibited. An amount exceeding 10% by weight makes a stiff water-/oil interface, which tends to make the resulting product feel heavy and sticky.

Water, component (J), is incorporated in an amount of 5-69.9% by weight.

In the preparation of the w/o-type emulsion cosmetic composition, the acryl-silicone graft copolymer (A), low-viscosity silicone oil (B) and/or low-boiling-point oil (D) are dissolved in advance. Otherwise, a process conventionally used for the production of a w/o-type emulsion cosmetic can be used for the preparation of the composition.

The cosmetic compositions provided by the present invention can be applied to a wide variety of uses such as for basic cosmetics, makeup cosmetics, hair cosmetics, and the like. Besides the above components various components conventionally used for cosmetics can be optionally incorporated into the cosmetic composition of the present invention to the extent that such incorporation does not impair the intended effects of the cosmetic composition. Such optional components include alkali metal soaps, polyhydric alcohols, high molecular weight compounds, preservatives, alkaline agents, UV absorbers, anti-oxidants, tar-derived coloring agents, skin-improvers, humectants, perfumes, and the like.

Other features of the invention will become apparent in the course of the following description of the exemplary embodiments which are given for illustration of the invention and are not intended to be limiting thereof.

EXAMPLES

Reference Example 1

Synthesis of acryl-silicone graft copolymer 35 g of a dimethylpolysiloxane having a methacrylate group on one of the molecular chain terminals and represented by the following formula,

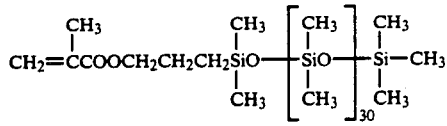

45 g of methylmethacrylate, 20 g of 2-ethyl-hexylacrylate, and 100 g of toluene were mixed. After an addition and dissolution of 1.5 g of azobisisobutyronitrile, the mixture was reacted for 5 hours at 80°-90° C. while stirring to obtain a viscous solution. The solution was charged into 2 l of methanol, thereby precipitating a graft copolymer. The precipitate was collected by filtration and dried to obtain 88 g of a white substance. The substance was confirmed by means of an infrared absorption spectrum to be a methacrylate copolymer in which dimethylpolysiloxane was grafted. The copolymer had a glass transition temperature of 37° C. and a weight average molecular weight of about 13,000, converted to polystyrene, by gel permeation chromatography (hereinafter abbreviated as "GPC") analysis.

REFERENCE EXAMPLE 2

Synthesis of acryl-silicone graft copolymer

The same procedure as in Reference Example 1 was performed using 25 g of a dimethylpolysiloxane having a methacrylate group on one of the molecular chain terminals represented by the following formula,

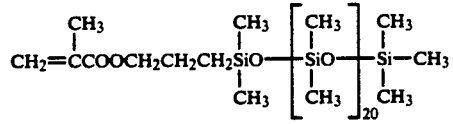

50 g of methylmethacrylate, 15 g of n-butylmethacrylate, and 10 g of vinyl acetate as starting materials to produce a graft copolymer. The copolymer had a glass transition temperature of 26° C. and a weight average molecular weight of about 11,000, converted to polystyrene, by GPC analysis.

REFERENCE EXAMPLE 3

Synthesis of acryl-silicone graft copolymer

The same procedure as in Reference Example 1 was performed using 30 g of a dimethylpolysiloxane having a methacrylate group on one of the molecular chain terminals represented by the following formula,

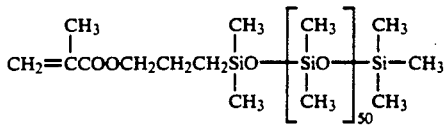

30 g of methylmethacrylate, and 40 g of n-butylmethacrylate as starting materials to produce 93 g of a graft copolymer. The copolymer was confirmed by means of an infrared absorption spectrum as a methacrylate copolymer in which dimethylpolysiloxane was grafted. The copolymer had a glass transition temperature of 18° C. and a weight average molecular weight of about 16,000, converted to polystyrene, by GPC analysis.

REFERENCE EXAMPLE 4

Synthesis of acryl-silicone graft copolymer

The same procedure as in Reference Example 1 was performed using 40 g of a dimethylpolysiloxane having a methacrylate group on one of the molecular chain terminals represented by the following formula,

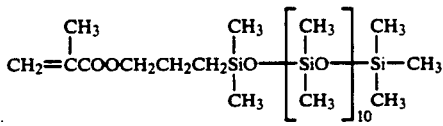

40 g of methylmethacrylate, and 20 g of 2-ethylhexylacrylate as starting materials to produce a graft copolymer. The copolymer had a glass transition temperature of 25° C. and a weight average molecular weight of about 15,000, converted to polystyrene, by GPC analysis.

REFERENCE EXAMPLE 5

Synthesis of acryl-silicone graft copolymer

The same procedure as in Reference Example 1 was performed using 35 g of a dimethylpolysiloxane having a methacrylate group on one of the molecular chain terminals represented by the following formula,

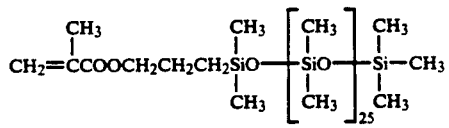

47 g of methylmethacrylate, and 18 g of 2-ethylhexylacrylate as starting materials to produce 88 g of a graft copolymer. The copolymer was confirmed by means of an infrared absorption spectrum as a methacrylate copolymer in which dimethylpolysiloxane was grafted. The copolymer had a glass transition temperature of 30° C. and a weight average molecular weight of about 15,000, converted to polystyrene, by GPC analysis.

EXAMPLE 1

Gel composition 35 g of the graft copolymer prepared in Reference Example 3 and 65 g of dimethylpolysiloxane having a viscosity of 6 cs at 25° C. [KF-96A (6 cs) (Trademark), manufactured by Shin-etsu Chemical Co., Ltd.]were dissolved in 150 g of isopropanol. Isopropanol was evaporated from the mixture at 60° C. under a pressure of 50 mmHg with stirring, thereby producing a gel composition as a uniform solid.

EXAMPLE 2

Gel composition

The same procedure as in Example 1 was performed using 40 g of the graft copolymer prepared in Reference Example 4 and 60 g of decamethylcyclopentasiloxane [KF-995 (Trademark), manufactured by Shin-etsu Chemical Co., Ltd.] to produce a gel composition as a uniform solid.

EXAMPLE 3

Gel composition

The same procedure as in Reference Example 1 was performed using 45 g of a dimethylpolysiloxane having a methacrylate group on one of the molecular chain terminals and represented by the following formula,

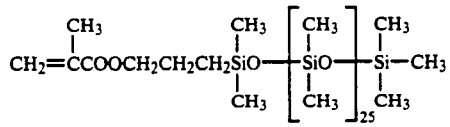

30 g of methylmethacrylate, and 10 g of n-buthylmethacrylate and 15 g of 2-ethyl-hexylacrylate as starting materials to produce a graft copolymer. The copolymer had a glass transition temperature of 20° C. and a weight average molecular weight of about 17,000, converted to polystyrene, by GPC analysis. Then, 30 g of the graft copolymer prepared above and 70 g of dimethylpolysiloxane (5 cs) [KF-96 (Trademark), manufactured by Shin-etsu Chemical Co., Ltd.] were processed according to the same procedure as in Example 1 to produce a gel composition as a uniform jelly.

EXAMPLE 4

Solid foundation

| <Formulation> | |
|---|---|
| | parts by weight |
| (1) Titanium dioxide | 12.0 |
| (2) Red iron oxide | 0.8 |
| (3) Yellow iron oxide | 1.8 |
| (4) Black iron oxide | 0.6 |
| (5) Liquid paraffin | 5.0 |
| (6) Gel composition prepared in Example 1 | 79.8 |

<Preparation>

After the components (1)–(5) were mixed and homogenized, the component (6) was added. The mixture was uniformly dispersed using a triple roll mill. The dispersed mixture was melted and charged into a container. The mixture in the container was cooled to solidify, thus obtaining a solid foundation.

COMPARATIVE EXAMPLE 1

Solid foundation

A solid foundation was produced according to the same method as in Example 4 by using, instead of the solid gel composition, which is component (6) in Example 4, a mixture of 12 parts by weight of Dextrine fatty acid ester and 67.8 parts by weight of liquid paraffin which was melted under heating.

The solid foundations thus produced, as well as the product produced in Example 4, were evaluated by panelists consisting of twenty women. In the evaluation, each product wa rated according to the following standard. The results are shown in Table 1.

| <Rating of Evaluation> | |
|---|---|
| Very good | 3 points |
| Good or Usual | 2 points |
| Bad | 1 point |
| <Evaluation Standard> | |
| Average total point | Standard |
| 2.5 or more | AAA |
| 2.0 or more but less than 2.5 | BBB |
| 1.5 or more but less than 2.0 | CCC |
| Less than 1.5 | DDD |

TABLE 1

| Evaluation | Inventive Example 4 | Comparative Example 1 |
|---|---|---|
| Freshness | AAA | BBB |
| Low stickiness | AAA | DDD |
| Spreadability | AAA | DDD |
| Resistance to water | AAA | BBB |
| Retentiveness of the make-up | AAA | BBB |

As shown in Table 1, the solid foundation to which the solid gel composition of the present invention was incorporated gave a better feeling upon use and was easier to use than the comparative foundation.

EXAMPLE 5

Stick eyeshadow

| <Formulation> | |
|---|---|
| | parts by weight |
| (1) Gel composition prepared in Example 2 | 75.0 |
| (2) Decamethylcyclopentasiloxane | 10.0 |
| (3) Colored pigment | 4.5 |
| (4) Titanated mica | 8.5 |
| (5) Mica | 2.0 |

<Preparation>

Components (1)–(5) were mixed. The mixture was kneaded with a triple roll mill to homogenize. The mixture was melted and charged into a container to obtain a stick eyeshadow.

The stick eyeshadow thus produced had excellent characteristics, including smoothness to the touch; good sreadability; non-sticky, fresh, sensation upon use; long makeup retentiveness; and high water-resistance.

A comparative stick eyeshadow was produced using 15 parts by weight of microcrystalline wax and 60 parts by weight of dimethylpolysiloxane (5 cs) instead of the component (1) in Example 5 using the same process as in Example 5. This stick eyeshadow was less spreadable and more sticky than the eyeshadow of Example 5. This comparative stick eyeshadow also exhibited instability over time, separating oil components during storage.

This example demonstrated that a stick eyeshadow which is very useful and has a high quality could be produced without using structural components, e.g. wax, according to this invention.

EXAMPLE 6

Hand cream (o/w-type)

| <Formulation> | parts by weight |
|---|---|
| (1) Stearic acid | 2.5 |
| (2) Cetyl alcohol | 1.7 |
| (3) Gel composition prepared in Example 1 | 10.0 |
| (4) Octamethylcyclotetrasiloxane | 10.0 |
| (5) Sorbitan sesquioleate | 1.0 |
| (6) Polyoxyethylene sorbitan monooleate | 2.0 |
| (7) Triethanolamine | 0.7 |
| (8) 1,3-butylene glycol | 5.0 |
| (9) Carboxyvinyl polymer | 0.5 |
| (10) Purified water | 66.6 |

<Preparation>

Components (1)–(6) were mixed and molten under heating at 80° C. to prepare an oil phase, while components (7)–(10) were mixed and dissolved under heating at 80° C. to prepare a water phase. The water phase was added to the oil phase with stirring to emulsify. After cooling, the emulsion was packed into a container, thus producing a hand cream.

The hand cream thus obtained exhibited a good, fresh sensation to the skin upon use without oiliness.

EXAMPLE 7

Face cream (w/o-type)

| <Formulation> | parts by weight |
|---|---|
| (1) Gel composition prepared in Example 2 | 6.0 |
| (2) Liquid paraffin | 20.0 |
| (3) Isoparaffin (IP Solvent 1620) | 6.0 |
| (4) Dipentaerythritol fatty acid ester | 2.0 |
| (5) Petrolatum | 4.0 |
| (6) Diglyceryl diisostearate | 2.0 |
| (7) Citric acid | 0.3 |
| (8) Sodium citrate | 1.2 |
| (9) 1,3-Butylene glycol | 8.0 |
| (10) Methyl paraoxybenzoate | 0.1 |
| (11) Purified water | 50.4 |

<Preparation>

Components (1)–(5) were mixed and molten under heating. To the mixture was added a gel emulsion which was prepared in advance by adding components (7)–(8), and a portion of component (11) to component (6). The mixture was heated to 70° C., and to this as added a mixture which was prepared by mixing components (9), (10), and the remaining portion of component (11) and molten with heating in advance, thus making an emulsion. The emulsion was cooled and packed into a container to produce a face cream.

The face cream thus obtained exhibited an excellent sensation to the skin upon use and high storage stability. It was very suitable for protecting the face skin.

EXAMPLE 8

Nail treatment

| <Formulation> | parts by weight |
|---|---|
| (1) Gel composition prepared in Example 1 | 50.0 |
| (2) Hydrophobic silicic anhydride | 2.0 |
| (3) Octamethylcyclotetrasiloxane | 38.0 |
| (4) Dimethylpolysiloxane (20cs) | 8.0 |
| (5) Sunscreen agent | 1.0 |
| (6) Perfume | q.s. |
| (7) Pigment | q.s. |

<Preparation>

Components (1)–(7) were mixed and sufficiently kneaded with a triple roll mill to produce a nail treatment.

The creamy nail treatment thus obtained exhibited a fresh sensation upon use without stickiness and gave a moderate gloss to the nail. It was very useful nail treatment.

EXAMPLE 9

Jelly-like solid eyeshadow

| <Formulation> | parts by weight |
|---|---|
| (1) Gel composition prepared in Example 3 | 65.0 |
| (2) Decamethylcyclopentasiloxane | 10.0 |
| (2) Hydrophobic silicic anhydride | 1.0 |
| (3) Colored pigment | 3.0 |
| (4) Iron oxide titanated mica | 5.5 |
| (5) Mica | 2.0 |
| (6) Dimethylpolysiloxane (10 cs) | 13.5 |
| (7) Perfume | q.s. |

<Preparation>

Components (1)–(8) were mixed. The mixture was kneaded with a triple roll mill to homogenize. The homogenized mixture was molten and charged into a container to obtain a jelly-like solid eyeshadow.

The jelly-like solid eyeshadow thus produced was elastic and had a fresh appearance. It exhibited high spreadability, fine sensation without stickiness upon use, and excellent makeup retentiveness.

REFERENCE EXAMPLE 6

Synthesis of partially cross-linked organopolysiloxane polymer 1,790 g of trimethylsilyl-terminal sealded-dimethyl methylhydrogenpolysiloxane (average molecular weight: 2,340, Si-H: 4.5 mol%) and 710 g of dimethyl-vinylsilyl-terminal sealded-dimethylpolysiloxane (average molecular weight: 930, vinyl group: 7.7 mol%) were charged into a planetarium mixer with an internal volume of about 5 l and were mixed with stirring. To the mixed solution was added 0.5 g of 2% isopropanol solution of chloro platinic acid. The mixture was heated to 70°-80° C. and stirring was continued for 2 hours. The pressure was reduced to 5-10 mmHg and stripping was carried out for 30 minutes, thus producing a colorless, flexible solid partially cross-linked organopolysiloxane polymer.

EXAMPLE 10

Paste-like lipstick

<Formulation>

| | parts by weight |
|---|---|
| (1) Red iron oxide | 0.8 |
| (2) FD&C Yellow No. 4 aluminum lake | 0.1 |
| (3) Red No. 202 (D&C Red No. 7) | 0.3 |
| (4) Iron oxide titanated mica | 15.0 |
| (5) Liquid paraffin | 3.8 |
| (6) Acryl-silicone graft copolymer*[1] | 20.0 |
| (7) Partially cross-linked organopolysiloxane polymer*[2] | 10.0 |
| (8) Dimethylpolysiloxane (10 cs) | 50.0 |

*[1] Copolymer obtained in Reference Example 3
*[2] Polymer obtained in Reference Example 6

<Preparation>

To components (6)–(8) which were mixed under heating were added components (1)–(5). After the mixture was kneaded with a triple roll mill to homogeneously disperse, it was packed into a container, followed by cooling to solidify, thus obtaining a paste-like lipstick. The paste-like lipstick of this invention was well spreadable on the lip. It gave an excellent sensation and fresh feeling upon use, and exhibited a long makeup retentiveness.

EXAMPLE 11

Stick eyeshadow

<Formulation>

| | parts by weight |
|---|---|
| (1) Colored Pigments | 1.36 |
| (2) Ultramarine blue | 3.5 |
| (3) Black iron oxide | 0.45 |
| (4) Titanated mica | 8.5 |
| (5) Mica | 2.19 |
| (6) Methylphenylpolysiloxane (10 cs) | 10.0 |
| (7) Acryl-silicone graft copolymer*[3] | 25.0 |
| (8) Partially cross-linked organopolysiloxane polymer*[4] | 4.9 |
| (9) Dimethylpolysiloxane (10 cs) | 44.1 |

*[3] Copolymer obtained in Reference Example 4
*[4] Polymer obtained in Reference Example 6

<Preparation>

To components (6)–(9) which were mixed under heating were added components (1)–(5). The mixture was kneaded with a triple roll mill to homogenize. The homogenized mixture was charged into a container, followed by cooling to solidify, thus producing a stick eye shadow.

EXAMPLE 12

Solid foundation

<Formulation>

| | parts by weight |
|---|---|
| (1) Titanium dioxide | 11.8 |
| (2) Red iron oxide | 0.8 |

-continued

<Formulation>

| | parts by weight |
|---|---|
| (3) Yellow iron oxide | 1.8 |
| (4) Black iron oxide | 0.6 |
| (5) Liquid paraffin | 5.0 |
| (6) Acryl-silicone graft copolymer*[5] | 30.0 |
| (7) Partially cross-linked organopolysiloxane polymer*[6] | 5.0 |
| (8) Dimethylpolysiloxane (5 cs) | 45.0 |

*[5] Copolymer obtained in Reference Example 3
*[6] Polymer obtained in Reference Example 6

<Preparation>

To components (6)–(8) which were mixed under heating were added components (1)–(5). The mixture was kneaded with a triple roll mill to obtain a homogenize. The homogeneous mixture was charged into a container, followed by cooling to solidify, thus producing a solid foundation.

EXAMPLE 13

Solid rouge

<Formulation>

| | parts by weight |
|---|---|
| (1) Red No. 226 (D&C Red No. 30) | 0.4 |
| (2) Red Iron oxide | 0.2 |
| (3) Ultramarine blue | 0.15 |
| (4) Mica | 30.0 |
| (5) Talc | 34.0 |
| (6) Methylphenylpolysiloxane (10 cs) | 3.25 |
| (7) Acryl-silicone graft copolymer*[7] | 12.5 |
| (8) Partially cross-linked organopolysiloxane polymer*[8] | 2.45 |
| (9) Dimethylpolysiloxane (10 cs) | 17.05 |

*[7] Copolymer obtained in Reference Example 3
*[8] Polymer obtained in Reference Example 6

<Preparation>

To components (6)–(9) which were mixed under heating were added components (1)–(5). After the mixture was kneaded with a triple roll mill and uniformly dispersed, it was packed into a container, followed by cooling to solidify, thus obtaining a solid rouge.

EXAMPLE 14

Eyeliner

<Formulation>

| | parts by weight |
|---|---|
| (1) Isoparaffin (IP Solvent 1620) | 46.0 |
| (2) Acryl-silicone graft copolymer prepared in Reference Example 1 | 30.0 |
| (3) Organic modified bentonite | 3.0 |
| (4) 1,3-butylene glycol | 1.0 |
| (5) Perfume | q.s. |
| (6) Colored pigment | 20.0 |

<Preparation>

Component (2) was dissolved in component (1). To this was added a mixture of components (3) and (4). Components (5) and (6) were added to the mixture. After the final mixture was kneaded with a triple roll mill and uniformly dispersed, it was packed into a container, thus obtaining an eyeliner.

COMPARATIVE EXAMPLE 2

Eyeliner

The same procedure as in Example 14 was performed using 5 parts by weight of microcrystalline wax and 25 parts by weight of pentaerythritol rhodinate instead of component (2) in Example 14 to produce an eyeliner.

The eyeliners of Example 14 and Comparative Example 2 were subjected to a durability test and sensory evaluation. The results are shown in Table 2.

Test specimens for the durability tests were prepared by applying the product to a nylon plate using a 6 mil doctor-blade to make a thin film of the product on the nylon plate followed by drying of the film. The water-resistance was evaluated by immersing a test specimen in water. The oil-resistance was evaluated by immersing a test specimen in an artificial sebum. The rubbing resistance was evaluated by rubbing the thin film with the fingers.

| <Evaluation standard> | |
|---|---|
| AAA: | Good |
| BBB: | Bad |

The sensory evaluation was performed by panelists consisting of twenty women. In the evaluation, each product was rated according to the following standard. The results are shown in Table 2.

| <Rating> | |
|---|---|
| Very good | 3 points |
| Good or Normal | 2 points |
| Bad | 1 point |

| <Evaluation Standard> | |
|---|---|
| Average total point | Standard |
| 2.5 or more | AAA |
| 2.0 or more but less than 2.5 | BBB |
| 1.5 or more but less than 2.0 | CCC |
| Less than 1.5 | DDD |

TABLE 2

| Evaluation | Inventive Example 14 | Comparative Example 2 |
|---|---|---|
| <Durability test> | | |
| Water Resistance | AAA | AAA |
| Oil Resistance | AAA | BBB |
| Rubbing Resistance | AAA | BBB |
| <Sensory evaluation> | | |
| Easiness of application | BBB | BBB |
| Inconsistency | BBB | BBB |
| Makeup Retentiveness | AAA | BBB |

As shown in Table 2, the eyeliner of this invention produced a film which was highly resistant to water and oil when applied. The eyeliner film also exhibited high resistance to rubbing and long makeup retentiveness.

EXAMPLE 15

Nail enamel

| <Formulation> | |
|---|---|
| | parts by weight |
| (1) Isoparaffin (Isoper-H) | 65.0 |
| (2) Acryl-silicone graft copolymer prepared in Reference Example 2 | 35.0 |
| (3) Colored pigment | q.s. |

<Preparation>

Component (2) was mixed with and dissolved in component (1). Component (3) was added to the mixture and uniformly dispersed. The final mixture was packed into a container to produce a nail enamel.

EXAMPLE 16

Mascara

| <Formulation> | |
|---|---|
| | parts by weight |
| (1) Isoparaffin (Isoper-H) | 52.0 |
| (2) Acryl-silicone graft copolymer prepared in Reference Example 1 | 25.0 |
| (3) Organic modified bentonite | 3.0 |
| (4) Paraffin wax | 5.0 |
| (5) Carnauba wax | 4.0 |
| (6) 1,3-Butylene glycol | 1.0 |
| (7) Perfume | q.s. |
| (8) Colored pigment | 10.0 |

<Preparation>

To a solution of component (1) in component (2) was added components (3)–(6). The mixture was molten under heating and components (7) and (8) were added to the molten mixture. The mixture thus obtained was uniformly kneaded with a triple roll mill and packed into a container to produce a mascara.

EXAMPLE 17

Eyeliner (Emulsion type)

| <Formulation> | |
|---|---|
| | parts by weight |
| (1) Stearic acid | 2.0 |
| (2) Cetanol | 0.5 |
| (3) Bees wax | 5.0 |
| (4) Sorbitan sesquioleate | 0.5 |
| (5) Polyethylene sorbitane monooleate (20 E.O.) | 0.5 |
| (6) Triethanolamine | 1.2 |
| (7) Colored pigment | 14.0 |
| (8) Polymethacrylic acid | 0.5 |
| (9) Acryl-silicone graft copolymer prepared in Reference Example 1 | 12.5 |
| (10) Isoparaffin (Isoper-H) | 12.5 |
| (11) Methyl paraoxybenzoate | 0.2 |
| (12) Purified water | 50.6 |

<Preparation>

Components (1)–(5) and (9)–(10) were mixed and dissolved under heating. To this were added components (6)–(8) and (11)–(12) which were dissolved with heating. After the mixture was emulsified and cooled, it was packed into a container, thus producing an eyeliner.

The products prepared in Examples 15, 16, and 17 produced films having superior resistance to water and oil. They also had the advantage of exhibiting good sensation upon use.

EXAMPLE 18

Eyeliner

Eyeliners having formulations shown in Table 3 were produced according to the processes described below. Water resistance, adhesiveness, oil-resistance, and makeup retentiveness of the eyeliners were evaluated by the test explained below. The results are shown in Table 4.

TABLE 3

| | <Formulation> % by weight | | |
|---|---|---|---|
| | Example | Comparative Example | |
| Component | 18 | 3 | 4 |
| (1) Stearic acid | | | 5.0 |
| (2) Cetanol | | | 0.5 |
| (3) Bees wax | | | 0.5 |
| (4) Sorbitan sesquioleate | | | 0.5 |
| (5) Polyoxyethylene sorbitan monooleate (20 E.O.) | | | 0.5 |
| (6) Colored pigment | 14.0 | 14.0 | 14.0 |
| (7) Ethyl polymethacrylate emulsion | | 25.0 | 25.0 |
| (8) Acryl-silicone graft copolymer*1 | 12.5 | | |
| (9) Isoparaffin*2 | 12.5 | | |
| (10) Polymethacrylic acid emulsion | 2.0 | 2.0 | |
| (11) Triethanolamine | 0.5 | 0.5 | 0.5 |
| (12) Methyl paraoxybenzoate | 0.2 | 0.2 | 0.2 |
| (13) Purified water | 58.3 | 58.3 | 53.3 |
| Total | 100.0 | 100.0 | 100.0 |

*1Acryl-silicone graft copolymer prepared in Reference Example 4
*2Isoper (Trademark, manufactured by Esso Chemical Co., Ltd.)

<Preparation>

EXAMPLE 18

Components (6), (10), (11), (12), and (13) were mixed under heating. The mixture was added to a mixture of components (8) and (9) while stirring and uniformly dispersed. The final mixture was cooled and packed into a container, thus producing an eyeliner.

COMPARATIVE EXAMPLE 3

Components (6), (10), (11), (12), and (13) were mixed under heating. The mixture was added to component (7) while stirring and uniformly dispersed. The final mixture was cooled and packed into a container, thus producing an eyeliner.

COMPARATIVE EXAMPLE 4

A mixture of components (1)–(5) were dissolved under heating, and components (6), (11), (12), and (13) were mixed under heating. The latter mixture was added to the former mixture to emulsify. Component (7) was added to the emulsion with stirring and dispersed. The mixture obtained was cooled and packed into a container, thus producing an eyeliner.

<Test method> a. Water Resistance

An appropriate amount of a sample was applied onto a glass plate to form a film having a prescribed thickness using a doctor-blade. After the sample on the glass plate was dried, it was immersed in water and shaken. The time required for the sample film to be released from the plate was taken as the water-resistance of the sample.

b. Adhesiveness

A sample was applied onto the wrist and dried. After 30 time curvature movements, the conditions of the sample on the wrist was observed to evaluate the adhesive force.

c. Oil Resistance

An appropriate amount of a sample was applied onto a glass plate to form a film with a prescribed thickness using a doctor-blade. After the sample on the glass plate was dried, an synthetic sebum was applied onto the film. After leaving the sample for a prescribed period of time, the surface of the sample was rubbed by fingers and the state of the surface was observed to evaluate the oil-resistance of the sample.

d. Makeup Retentiveness

The sample was subjected to an actual using test to compare their makeup retentiveness

| <Evaluation standard> The results of measurement in above tests a–d were evaluated according to the following standard. | |
|---|---|
| AAA: | very good |
| BBB: | good |
| CCC: | a bit worse |
| DDD: | bad |

TABLE 4

| | Example | Comparative Example | |
|---|---|---|---|
| | 18 | 3 | 4 |
| Water-resistance | AAA | DDD | CCC |
| Adhesive force | AAA | BBB | BBB |
| Oil-resistance | BBB | CCC | CCC |
| Retentiveness of the makeup | AAA | CCC | CCC |

As shown in Table 4, the eyeliner of the present invention exhibited more excellent water-resistance, adhesiveness, and oil-resistance, as well as makeup retentiveness than the comparative eyeliners. The eyeliner of this invention had also advantages of good spreadability to form a uniform film, fine sensation upon use, and long makeup retentiveness.

EXAMPLE 19

Mascara

| <Formulation> | |
|---|---|
| | parts by weight |
| (1) Candelilla Wax | 2.0 |
| (2) Paraffin wax | 2.0 |
| (3) Bees wax | 3.0 |
| (4) Isopropyl myristate | 2.0 |
| (5) Sorbitan sesquioleate | 0.5 |
| (6) Colored pigment | 10.0 |
| (7) Acryl-silicone graft copolymer*3 | 15.0 |
| (8) Isoparaffin*4 | 15.0 |
| (9) Dimethylpolysiloxane*5 | 5.0 |
| (10) Polymethacrylic acid emulsion | 2.5 |
| (11) Triethanolamine | 0.7 |

-continued

| <Formulation> | |
|---|---|
| | parts by weight |
| (12) Methyl paraoxybenzoate | 0.2 |
| (13) Purified water | 42.1 |
| Total | 100.0 |

*³Acryl-silicone graft copolymer prepared in Reference Example 1
*⁴Isoper-H (Trademark, manufactured by Esso Chemical Co., Ltd.)
*⁵Silicone KF994 (Trademark, manufactured by Shin-etsu Chemical Co., Ltd.

<Preparation>

Components (1)–(5) were mixed and heated to melt. To the molten mixture was added a mixture of components (7)–(9) and uniformly dispersed. Components (6), (10), (11), (12), and (13) were mixed under heating and added to the former mixture while stirring and uniformly dispersed. The final mixture was cooled and packed into a container, thus producing a mascara.

The mascara thus obtained exhibited good usability, e.g. good spreadability, and high water- and oil-resistance, and good adhesiveness. The mascara of this invention had also advantages of good makeup, fine sensation upon use, and high stability over time.

EXAMPLE 20 AND EXAMPLE 21

Cream cosmetic (o/w-type)

Creams having formulations shown in Table 5 were produced according to the process described below. The water-repellency, oiliness, stickiness of each composition were evaluated by the test methods explained below.

TABLE 5

| | (parts by weight) | | | | | | |
|---|---|---|---|---|---|---|---|
| | Example | | Comparative Example | | | | |
| Component | 20 | 21 | 5 | 6 | 7 | 8 | 9 |
| (1) Stearic acid | 2.0 | 2.0 | 2.0 | 2.0 | 2.0 | 2.0 | 2.0 |
| (2) Cetanol | 1.5 | 1.5 | 1.5 | 1.5 | 1.5 | 1.5 | 1.5 |
| (3) Lipophilic glycerol monostearate | 1.5 | 1.5 | 1.5 | 1.5 | 1.5 | 1.5 | 1.5 |
| (4) Sorbitan monostearate | 0.5 | 0.5 | 0.5 | 0.5 | 0.5 | 0.5 | 0.5 |
| (5) Polyoxyethylene sorbitan monooleate (20 E.O.) | 0.5 | 0.5 | 0.5 | 0.5 | 0.5 | 0.5 | 0.5 |
| (6) Acryl-silicone graft copolymer (prepared in Ex. 1) | 6.0 | 10.0 | 0.2 | 5.0 | 1.0 | 5.0 | 1.0 |
| (7) Light liquid paraffin¹ | 10.0 | 10.0 | 12.8 | — | 15.0 | 5.0 | 1.0 |
| (8) Decamethylcyclopentasiloxane | — | 5.0 | 4.0 | 15.0 | 2.0 | 10.0 | 0.5 |
| (9) Glyceryl trioctanate | 4.0 | 5.0 | 3.0 | 10.0 | 2.0 | 10.0 | 0.5 |
| (10) Triethanolamine | 1.5 | 1.5 | 1.5 | 1.5 | 1.5 | 1.5 | 1.5 |
| (11) 1,3-butylene glycol | 10.0 | 10.0 | 10.0 | 10.0 | 10.0 | 10.0 | 10.0 |
| (12) Purified water | 62.5 | 52.5 | 62.5 | 52.5 | 62.5 | 52.5 | 79.5 |
| ²Total amount of oil component | 20 | 30 | 20 | 30 | 20 | 30 | 3 |
| Ratio of (A)/Total oil component | 30 | 33.3 | 1 | 16.6 | 5 | 16.6 | 33.3 |
| Ratio of (B)/Total oil component | 50 | 33.3 | 64 | 0 | 75 | 16.6 | 33.3 |
| Ratio of (A) + (B)/Total oil component | 80 | 66.6 | 65 | 16.6 | 80 | 33.3 | 66.6 |

¹IP solvent 1620 (Trademark), produced by Idemitsu Petrochemical Co., Ltd.
²(A): Total amount of components (6)–(8)  (B): Total amount of components (1)–(5) and (9)

<Preparation>

Components (6)–(8) were homogeneously mixed. To the mixture was added a mixture of components (1)–(5) and (9) which was molten with heating, and the whole mixture was heated to 70° C. Components (10)–(12) were mixed and heated to 70° C., and were added to the former mixture while stirring to emulsify. The final mixture was cooled to produce a cream.

<Test method>

Water Repellency

A cream was applied onto a glass plate to form a film 0.02 mm thick. The film sample was left for 24 hours in a thermo-hygrostat at a temperature of 35° C. and 25% humidity to obtain a dry film. 0.2 ml of purified water was dropped onto the film from a height of 1 cm. The area on the film in which the water diffused was measured and taken as the water-repellency of the cream.

| <Evaluation Standard> | | |
|---|---|---|
| Expression | Evaluation | Water diffusion area |
| AAA | Good | Smaller than 100 mm² |
| BBB | Normal | 100 mm² to 200 mm² |
| CCC | Bad | Greater than 200 mm² |

<Sensory evaluation for oiliness and stickiness>

The sensory evaluation was performed by panelists consisting of 30 women. In the evaluation, each product was rated according to the following standard. The results are shown in Table 6.

| <Rating of Evaluation> | |
|---|---|
| Very good | 3 points |
| Good or Normal | 2 points |
| Bad | 1 points |

<Evaluation Standard>

| Average total point | Standard |
|---|---|
| 2.5 or more | AAA |
| 2.0 or more but less than 2.5 | BBB |
| 1.5 or more but less than 2.0 | CCC |
| Less than 1.5 | DDD |

TABLE 6

| Item of Evaluation | Example 20 | Example 21 | Comparative Example 5 | Comparative Example 6 | Comparative Example 7 | Comparative Example 8 | Comparative Example 9 |
|---|---|---|---|---|---|---|---|
| Water repellency | BBB | BBB | DDD | CCC | DDD | BBB | DDD |
| Sensory evaluation | | | | | | | |
| Oillessness | AAA | AAA | BBB | AAA | BBB | BBB | AAA |
| Stickilessness | AAA | AAA | AAA | AAA | AAA | BBB | AAA |

As shown in Table 6, the cosmetics of Example 20 and 21 exhibited better results in water-repellency and sensory evaluation than Comparative Examples 5-8. Further, the cosmetics of Examples 20 and 21 produced a flexible and tight film.

EXAMPLE 22

Acidic cream (o/w-type)

<Formulation>

| | parts by weight |
|---|---|
| (1) N-stearoyl-L-glutamate | 0.2 |
| (2) Cetanol | 2.0 |
| (3) Lipophilic glycerol monostearate | 2.0 |
| (4) Isoparaffin (Isoper-H: Trademark, manufactured by Esso Chemical Co.) | 11.0 |
| (5) Decamethylcyclopentasiloxane | 4.0 |
| (6) Acryl-silicone graft copolymer prepared in Reference Example 2 | 8.0 |
| (7) Liquid paraffin | 3.5 |
| (8) Glyceryl octanoate | 3.5 |
| (9) Polyoxyethylene sorbitan monooleate (20 E.O.) | 0.5 |
| (10) Sorbitan sesquioleate | 0.3 |
| (11) Perfume | 0.1 |
| (12) Sodium hydroxide | 0.02 |
| (13) 1,3-Butylene glycol | 8.0 |
| (14) Methyl paraoxybenzoate | 0.1 |
| (15) Carboxy-vinyl polymer | 0.05 |
| (16) purified water | 56.73 |
| Total amount of oil components | 30 Wt % |
| Ratio of (A)/total oil components | 26.7 Wt % |
| Ratio of (B)/total oil components | 36.7 Wt % |
| Ratio of [(A) + (B)]/total oil components | 63.4 Wt % |

(A): Total amount of components (4), (5), (6)
(B): Total amount of components (1)–(3), (7)–(10)

<Preparation>

Component (6) was dissolved in components (4) and (5). To the mixture was added a mixture of components (1)–(3), and (7)–(10) which were mixed and heated to melt, and the whole mixture was heated to 70° C. Components (12)–(16) were mixed, dissolved under heating and heated to 70° C. This solution was added to the former mixture while stirring to emulsify. Component (11) was added to the emulsion, followed by cooling, thus producing an acidic cream.

The cream gave excellent sensation upon use, exhibited water-repellency, and was stable over a prolonged time period.

EXAMPLE 23

Sun-cut milky lotion (o/w-type emulsion cosmetic)

A sun-cut milky lotion having the following formulation was prepared according to the process described below.

<Formulation>

| | parts by weight |
|---|---|
| (1) N-stearoyl-L-glutamate | 0.2 |
| (2) Stearyl alcohol | 0.5 |
| (3) Lipophilic glycerol monostearate | 0.5 |
| (4) Isoparaffin (IP Solvent 1620: Trade name, manufactured by Idemitsu Petrochemical Co., Ltd.) | 7.8 |
| (5) Acryl-silicone graft copolymer prepared in Reference Example 1 | 3.2 |
| (6) Glyceryl trioctanoate | 2.5 |
| (7) Escarol 507 (Trade name, manufactured by Van Dyk Co., Ltd.) | 3.5 |
| (8) Oxybenzone | 1.0 |
| (9) Methyl paraoxybenzoate | 0.1 |
| (10) Sorbitan monostearate | 0.2 |
| (11) Sorbitan sesquioleate | 0.2 |
| (12) Perfume | 0.1 |
| (13) Sodium hydroxide | 0.02 |
| (14) Titanium dioxide | 0.5 |
| (15) 1,3-Butylene glycol | 13.3 |
| (16) Soybean phospholipid | 0.02 |
| (17) Carboxyvinyl polymer | 0.12 |
| (18) purified water | 66.35 |
| Total amount of oil components | 13.5 Wt % |
| Ratio of (A)/total oil components | 23.7 Wt % |
| Ratio of (B)/total oil components | 57.8 Wt % |
| Ratio of [(A) + (B)]/total oil components | 81.5 Wt % |

(A): Total amount of components (4), (5)
(B): Total amount of components (1)–(3), (6)–(11)

<Preparation>

Components (1)–(3) and (7)–(11) were mixed and heated to melt. To the mixture were added component (5) which was dissolved in component (4) and then component (6), and the whole mixture was heated to 70° C. Components (13)–(18) were mixed under heating at 70° C. and added to the former mixture with stirring to obtain an emulsion. The emulsion was cooled to produce a sun-cut milky lotion.

The lotion thus prepared gave excellent sensation upon use, exhibited water-repellency, and was stable over a prolonged time period.

EXAMPLE 24

Liquid foundation (non-aqueous-type makeup cosmetic)

Liquid foundations having formulations shown in Table 7 were produced according to the process described below. The foundations were evaluated and compared. The results are shown in Table 8.

TABLE 7

<Formulation>

| | % by weight | | | |
|---|---|---|---|---|
| | Example | Comparative Examples | | |
| Component | 24 | 10 | 11 | 12 |
| (1) Acryl-silicone graft | 15.0 | — | 15.0 | 15.0 |

TABLE 7-continued

| | <Formulation> | | | |
|---|---|---|---|---|
| | | % by weight | | |
| | Example | Comparative Examples | | |
| Component | 24 | 10 | 11 | 12 |
| copolymer (prepared in Reference Example 5) | | | | |
| (2) Pentaerythritol rhodinate | — | 5.0 | — | — |
| (3) Bees wax | — | 10.0 | — | 0.5 |
| (4) Dimethylpolysiloxane (5 cs) | 9.0 | 9.0 | 9.0 | — |
| (5) Methylphenylopolysiloxane | 5.0 | 5.0 | 5.0 | — |
| (6) Octamethylcyclotetrasiloxane | — | — | 40.0 | — |
| (7) Isoparaffin (Trademark: IP solvent 1620) | 40.0 | 40.0 | — | 54.0 |
| (8) Hydrophobic silicic anhydride | 1.0 | 1.0 | 1.0 | 1.0 |
| (9) Organic modified bentonite | 2.7 | 2.7 | 2.7 | 2.7 |
| (10) Dextrin fatty acid ester | 2.0 | 2.0 | 2.0 | 2.0 |
| (11) 1,3-Butylene glycol | 0.3 | 0.3 | 0.3 | 0.3 |
| (12) Titanium dioxide | 9.0 | 9.0 | 9.0 | 9.0 |
| (13) Inorganic colored pigment | 3.8 | 3.8 | 3.8 | 3.8 |
| (14) Nylon powder | 0.2 | 0.2 | 0.2 | 0.2 |
| (15) Talc | 4.0 | 4.0 | 4.0 | 4.0 |
| (16) Mica | 7.0 | 7.0 | 7.0 | 7.0 |
| (17) Titanated mica | 0.5 | 0.5 | 0.5 | 0.5 |
| (18) Lecithin | 0.5 | 0.5 | 0.5 | 0.5 |

<Preparation>

Components (1)–(7) were mixed and heated to melt. Components (8)–(18) were added to the molten mixture. The mixture obtained was uniformly kneaded by a triple roll mill and packed into a container, thus producing a liquid foundation.

| <Evaluation standard> | |
|---|---|
| AAA: | very good |
| BBB: | good |
| CCC: | a bit worse |
| DDD: | bad |

TABLE 8

| | Example | Comparative Example | | |
|---|---|---|---|---|
| Evaluated Items | 24 | 10 | 11 | 12 |
| Easiness of makeup | BBB | BBB | BBB | BBB |
| Smoothness | AAA | BBB | BBB | AAA |
| Oillessness | AAA | BBB | BBB | AAA |
| Non-consistency of the cosmetic film | BBB | BBB | BBB | DDD |
| Sweat/sebum resistance | AAA | BBB | AAA | AAA |
| Rubbing resistance | BBB | DDD | DDD | DDD |

As shown in Table 8, the non-aqueous foundation of this invention had an advantage of excellent characteristics over the comparative foundations of Comparative Examples 10–12, in terms of oilless, smooth and fine sensation upon use, formation of a film having a consistent feeling, high sweat-and sebum resistance which can well protect the makeup, strong rubbing resistance, and long makeup retentiveness.

EXAMPLE 25

Two-layer foundation (non-aqueous makeup)

A two-layer foundation having the following formulation was prepared according to the process described below.

| <Formulation> | |
|---|---|
| | parts by weight |
| (1) Acryl-silicone graft copolymer prepared in Reference Example 5 | 20.0 |
| (2) Dimethylpolysiloxane (5 cs) | 15.0 |
| (3) Isoparaffin (Isoper H) | 49.0 |
| (4) Hydrophobic silicic anhydride | 2.0 |
| (5) Titanium dioxide | 8.0 |
| (6) Inorganic colored pigment | 3.0 |
| (7) Mica | 2.9 |
| (8) Perfume | 0.1 |

<Preparation>

Components (1) was mixed with components (2) and (3) and dissolved. To the mixture were added components (4)–(8). The mixture thus obtained was kneaded by a triple roll mill to uniformly disperse and packed into a container, thus producing a non-aqueous and two-layer foundation with powder as sublayer.

The non-aqueous and two-layer foundation of this invention had an advantage of excellent characteristics, e.g. oilless sensation upon use without stickiness, formation of a makeup film having high water-, sweat-, oil- and sebum resistance, strong rubbing-resistance, and good makeup retentiveness.

EXAMPLE 26

Cream foundation (non-aqueous makeup)

A cream foundation having the following formulation was prepared according to the process described below.

| <Formulation> | |
|---|---|
| (1) Acryl-silicone graft copolymer prepared in Reference Example 5 | 13.0 |
| (2) Dimethylpolysiloxane (10 cs) | 20.0 |
| (3) Isoparaffin (IP Solvent 1620) | 40.0 |
| (4) Dextrin fatty acid ester | 2.0 |
| (5) Aluminum isostearate | 2.0 |
| (6) Organic modified bentonite | 0.5 |
| (7) Propylene glycol | 0.2 |
| (8) Titanium dioxide | 8.0 |
| (9) Inorganic colored pigment | 3.5 |
| (10) Titanated mica | 1.0 |
| (11) Lecithin | 0.8 |
| (12) Talc | 4.0 |
| (13) Mica | 5.0 |

<Preparation>

Components (1)–(7) were mixed and dissolved under heating. To the mixture were added components (8)–(13). The mixture thus obtained was kneaded with a triple roll mill to uniformly disperse and packed into a container, thus producing a non-aqueous cream foundation.

The non-aqueous cream foundation thus obtained was handy and easy to use, and gave an excellent sensation upon use with no sense of incongruity. Furthermore, the makeup film produced using this cosmetic had good characteristics such as high sweat- and sebum resistance, strong rubbing-resistance, and good makeup retentiveness.

EXAMPLE 27

Cream eyeshadow (non-aqueous makeup)

A cream eyeshadow having the following formulation was prepared according to the process described below.

| <Formulation> | |
|---|---|
| | parts by weight |
| (1) Acryl-silicone graft copolymer prepared in Reference Example 1 | 25.0 |
| (2) Dimethylpolysiloxane (5 cs) | 5.0 |
| (3) Isoparaffin (IP Solvent 1620) | 49.9 |
| (4) Dextrin fatty acid ester | 4.0 |
| (5) Hydrophobic silicic anhydride | 3.0 |
| (6) Inorganic colored pigment | 5.0 |
| (7) Titanated mica | 5.0 |
| (8) Mica | 3.0 |
| (9) Perfume | 0.1 |

<Preparation>

Components (1)–(4) were mixed and dissolved under heating. To the mixture were added components (5)–(9). The mixture thus obtained was kneaded by a triple roll mill to uniformly disperse and packed into a container, thus producing a cream eyeshadow.

The cream eyeshadow thus obtained gave a fine sensation upon use and exhibited good makeup retentiveness.

EXAMPLE 28 AND EXAMPLE 29

Creamy emulsion compositions (w/o-type) having a formulation shown in Table 9 were prepared according to the process described below. The stability of each composition was evaluated. The results are shown in Table 10.

TABLE 9

| <Formulation> | | | | | |
|---|---|---|---|---|---|
| | % by weight | | | | |
| | Example | | Comparative Example | | |
| Component | 28 | 29 | 10 | 11 | 12 |
| (1) Ocatamethylcyclotetrasiloxane | 6 | 6 | 6 | 12 | 12 |
| (2) Decamethylcyclopentasiloxane | 26 | 26 | 26 | 26 | 26 |
| (3) Acryl-silicone graft copolymer (prepared in Reference Example 3) | 6 | 6 | 6 | — | — |
| (4) Oxyalkylene modified organosiloxane *1 | 2 | — | — | 2 | — |
| (5) Hydroxyalkylene modified organosiloxane *2 | — | 2 | — | — | — |
| (6) Diglyceryl diisostearate | — | — | 2 | — | 2 |
| (7) Citric acid | 0.3 | 0.3 | 0.3 | 0.3 | 0.3 |
| (8) Sodium citrate | 1.2 | 1.2 | 1.2 | 1.2 | 1.2 |
| (9) 1,3-Butylene glycol | 5 | 5 | 5 | 5 | 5 |
| (10) Preservative | 0.1 | 0.1 | 0.1 | 0.1 | 0.1 |
| (11) Perfume | 0.1 | 0.1 | 0.1 | 0.1 | 0.1 |
| (11) Purified water | 53.3 | 53.3 | 53.3 | 53.3 | 53.3 |

*1: a = 20–30, b = 1–5, m = 2–5, n = 0, $R^1$ = H in formula (I)
*2: a = 2–10, b = 1–10, c = 20–60, m = 2–10, n = 0, $R^1$ = H, and $R^2$ = an alkyl group of a $C_{16}$ atom content in formula (I)

<Preparation>

Components (7), (8), and a solution of a portion of component (12) were slowly added to components (4)–(6), and mixed with stirring to prepare a gel composition. The mixture was added to a mixture of components (1)–(3) which were homogeneously dissolved, and the mixture was heated to 70° C. Components (9), (10), and the remaining portion of component (12) were mixed and dissolved and heated to 70° C. The latter mixture was added to the former mixture to emulsify. To the emulsion was added component (11) and the final mixture was cooled to obtain a w/o-type emulsion composition.

<Evaluation>

The emulsion composition thus obtained was left in a thermostats of temperatures of 50° C., 40° C., and 5° C. The states of the compositions after 1 week, 2 weeks, and 4 weeks were observed and evaluated according to the following standard.

| <Evaluation standard> | |
|---|---|
| AAA: | No change was observed |
| BBB: | Separation was slight and agglomeration occurred |
| CCC: | Separation was clear and agglomeration occurred |

TABLE 10

| | Example | | Comparative Example | | |
|---|---|---|---|---|---|
| | 28 | 29 | 13 | 14 | 15 |
| Next day | | | | | |
| 50° C. | AAA | AAA | CCC | AAA | AAA |
| 40° C. | AAA | AAA | CCC | AAA | AAA |
| 5° C. | AAA | AAA | AAA | AAA | AAA |
| After 1 week | | | | | |
| 50° C. | AAA | AAA | CCC | CCC | CCC |
| 40° C. | AAA | AAA | CCC | CCC | BBB |
| 5° C. | AAA | AAA | BBB | AAA | AAA |
| After 2 weeks | | | | | |
| 50° C. | AAA | AAA | CCC | CCC | CCC |
| 40° C. | AAA | AAA | CCC | CCC | CCC |
| 5° C. | AAA | AAA | CCC | AAA | AAA |
| After 4 weeks | | | | | |
| 50° C. | AAA | AAA | CCC | CCC | CCC |
| 40° C. | AAA | AAA | CCC | CCC | CCC |
| 5° C. | AAA | AAA | CCC | BBB | BBB |

As shown in Table 10, the w/o-type emulsion composition of this invention exhibited high stability without any change in the above conditions. As compared with the composition of the present invention, the comparative compositions had a disadvantage of separation, especially at high temperatures, and thus was unstable.

Furthermore, the emulsion composition of the present invention exhibited fine sensation upon use with no oily stickiness and well fitted to the skin. The cosmetic film after the makeup exhibited high water-repellency.

EXAMPLE 30

Face cream (w/o-type)

A face cream having the following formulation was prepared according to the process described below.

| <Formulation> | |
|---|---|
| | parts by weight |
| (1) Dimethylpolysiloxane (5 cs) | 12.0 |
| (2) Octamethylcyclotetrasiloxane | 15.0 |
| (3) Acryl-silicone graft copolymer prepared in Reference Example 4 | 5.0 |
| (4) Bees wax | 5.0 |
| (5) Petrolatum | 2.0 |
| (6) Lanolin | 3.0 |
| (7) Glyceryl trioctanoate | 2.0 |

-continued

| <Formulation> | |
|---|---|
| | parts by weight |
| (8) Hydroxyalkylene modified organopolysiloxane* | 2.0 |
| (9) Trisodium phosphate | 0.3 |
| (10) 1,3-Butylene glycol | 7.0 |
| (11) Perfume | q.s. |
| (12) Xanthan gum | 0.05 |
| (13) Sunscreen agent | q.s. |
| (14) Purified water | 46.65 |

*a = 2-10, b = 1-10, c = 20-60, m = 2-10, n = 0, p = 3, $R^1$ = H, and $R^2$ = an alkyl group of a $C_{16}$ atom content in formula (V)

<Preparation>

Components (1)–(8), (11), and (12) were mixed and homogenized at 75° C. Components (9), (10), (13), and (14) were mixed and dissolved at 75° C. The latter mixture was added to the former mixture to emulsify. The emulsion was cooled, thus producing a face cream.

The face cream thus obtained gave an excellent sensation upon use and exhibited high stability over time. Also, the face cream could form a water-repellent cosmetic film.

EXAMPLE 31

Hand cream (w/o-type)

A hand cream having the following formulation was prepared according to the process described below.

| <Formulation>.ls1 | |
|---|---|
| | parts by weight |
| (1) Dimethylpolysiloxane (5 cs) | 12.5 |
| (2) Decamethylcyclopentasiloxane | 15.0 |
| (3) Dimethylpolysiloxane (20 cs) | 2.5 |
| (4) Acryl-silicone graft copolymer prepared in Reference Example 4 | 15.0 |
| (5) Dipentaerythritol fatty acid ester | 4.5 |
| (6) Lanolin | 2.5 |
| (7) Glyceryl trioctanoate | 3.0 |
| (8) Hydroxyalkylene modified organopolysiloxane* | 2.0 |
| (9) Citric acid | 0.3 |
| (10) Sodium citrate | 1.2 |
| (11) 1,3-Butylene glycol | 5.0 |
| (12) Preservative | Slight amount |
| (11) Perfume | Slight amount |
| (12) Tocopherol acetate | Slight amount |
| (13) Purified water | 36.5 |

*a = 2-10, b = 1-10, c = 20-60, m = 2-10, n = 0, n = 3, $R^1$ = H, and $R^2$ = an alkyl group of a $C_{16}$ atom content in formula (V)

<Preparation>

Components (1)–(8), (13), and (14) were mixed and homogenized at 70° C. Components (9)–(12), and (15) were mixed and dissolved at 70° C. The latter mixture was added to the former mixture with stirring to emulsify. The emulsion was cooled, thus producing a hand cream.

The hand cream thus obtained could form a water-repellent film. The hand cream gave excellent sensation upon use with no oiliness, and exhibited good spreadability over the skin and high stability over time with no change in its outward appearance.

Obviously, numerous modifications and variations of the present invention are possible in light of the above teachings. It is therefore to be understood that within the scope of the appended claims, the invention may be practiced otherwise than as specifically described herein.

What is claimed is:

1. A cosmetic composition, comprising:
   (A) an acryl-silicone graft copolymer prepared by radically polymerizing (i) a dimethylpolysiloxane compound of the formula:

$$CH_2=\overset{R^1}{\underset{}{C}}-\underset{\underset{O}{\|}}{C}-O-R^2-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_l-\underset{\underset{CH_3}{|}}{\overset{\overset{CH_3}{|}}{Si}}-CH_3 \quad (I)$$

wherein $R^1$ is methyl or hydrogen, $R^2$ is a divalent, linear or branched $C_{1-10}$ hydrocarbon group optionally containing one or two ether bonds therein and l is a value of 3–300 and (ii) a radially polymerizable monomer comprising as a major component an acrylate monomer, a methacrylate monomer or combinations thereof, wherein the ratio of (i) to (ii) in the copolymer ranges from 1:19–2:1; and at least one component selected from the group consisting of (B) a low-viscosity silicone oil,
   (D) a low boiling-point oil,
   (E) a volatile solvent, and
   (H) a volatile hydrocarbon.

2. A cosmetic composition comprising:
   (A) an acryl-silicone graft copolymer which is prepared by radially polymerizing (i) a dimethylpolysiloxane compound of the formula:

$$CH_2=\overset{R^1}{\underset{}{C}}-\underset{\underset{O}{\|}}{C}-O-R^2-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_l-\underset{\underset{CH_3}{|}}{\overset{\overset{CH_3}{|}}{Si}}-CH_3 \quad (I)$$

wherein $R^1$ is methyl or hydrogen, $R^2$ is a divalent, linear or branched $C_{1-10}$ hydrocarbon group optionally containing one or two ether bonds therein and l is a value of 3–300 and (ii) a radially polymerizable monomer comprising as a major component an acrylate monomer, a methacrylate monomer or combinations thereof, wherein the ratio of (i) to (ii) ranges from 1:19–2:1; and (B) a low-viscosity silicone oil, wherein the weight ratio of component (A) to (B) ranges from 5:95–70:30.

3. A cosmetic composition comprising 30–100% by weight of a gel composition comprising:
   (A) 5–60% by weight of an acryl-silicone graft copolymer prepared by radically polymerizing (i) a dimethylpolysiloxane compound of the formula:

$$CH_2=\overset{R^1}{\underset{}{C}}-\underset{\underset{O}{\|}}{C}-O-R^2-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_l-\underset{\underset{CH_3}{|}}{\overset{\overset{CH_3}{|}}{Si}}-CH_3 \quad (I)$$

wherein $R^1$ is methyl or hydrogen, $R^2$ is a divalent, linear or branched $C_{1-10}$ hydrocarbon group optionally containing one or two ether bonds therein and l is a value of 3–300 and (ii) a radially polymerizable monomer comprising as a major component an acrylate monomer, a methacrylate monomer or combinations thereof, wherein the ratio of (i) to (ii) in the copolymer ranges from 1:19-2:1;

(B) 30-94.8% by weight of a low-viscosity silicone oil, and (C) 0.2-40% by weight of a partially cross-linked organopolysiloxane polymeric compound.

4. A cosmetic composition comprising:

(A) 10-70 wt.% of an acryl-silicone graft copolymer prepared by radially polymerizing (i) a dimethylpolysiloxane compound of the formula:

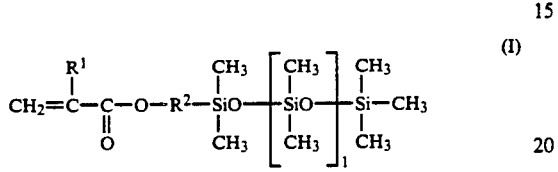

wherein $R^1$ is methyl or hydrogen, $R^2$ is a divalent, linear or branched $C_{1-10}$ hydrocarbon group optionally containing one or two ether bonds therein and 1 is a value of 3-300 and (ii) a radically polymerizable monomer comprising as a major component an acrylate monomer, a methacrylate monomer or combinations thereof, wherein the weight ratio of component (i) to component (ii) ranges from 1:19-2:1;

(D) a low-boiling-point oil; and (E) a volatile solvent.

5. An eye makeup cosmetic composition comprising:

(A) 5-20 wt.% of an acryl-silicone graft copolymer which is prepared by radically polymerizing (i) a dimethylpolysiloxane compound of the formula:

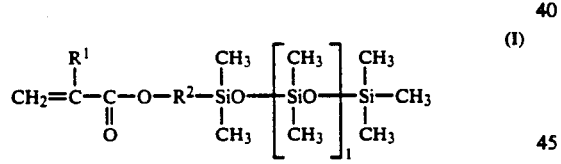

wherein $R^1$ is methyl or hydrogen, $R^2$ is a divalent, linear or branched $C_{1-10}$ hydrocarbon group optionally containing containing one or two ether bonds therein and 1 is a value of 3-300 and (ii) a radically polymerizable monomer comprising as a major component an acrylate monomer, a methacrylate monomer or combinations thereof, wherein the weight ratio of (i) to (ii) ranges from 1:19-2:1;

(D) 5-30 wt.% of a low-boiling-point oil;

(F) 5-40 wt.% of a cosmetic powder material; and (G) 1-10 wt.% of a polyacrylic emulsion of the type that increases its viscosity in alkaline conditions.

6. An oil-in-water emulsion cosmetic composition comprising 10-40% by weight of oily components which comprise:

(A) 2-40% by weight of an acryl-silicone graft copolymer which is prepared by radically polymerizing (i) a dimethylpolysiloxane compound of the formula:

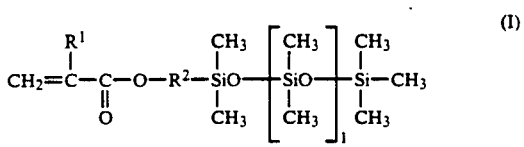

wherein $R^1$ is methyl or hydrogen, $R^2$ is a divalent, linear or branched $C_{1-10}$ hydrocarbon group optionally containing one or two ether bonds therein and 1 is a value of 3-300 and (ii) a radically polymerizable monomer comprising as a major component an acrylate monomer, a methacrylate monomer, or combinations thereof, wherein the ratio of (i) to (ii) in the copolymer ranges from 1:19-2:1; and (D) 20-60% by weight of a low-boiling-point oil, provided that the amount of components (A) plus (D) in the total oily component is 60-100% by weight.

7. A makeup cosmetic composition comprising:

(A) an acryl-silicone graft copolymer prepared by radically polymerizing (i) a dimethylpolysiloxane compound of the formula:

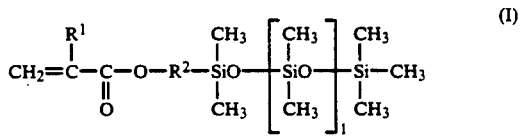

wherein $R^1$ is methyl or hydrogen, $R^2$ is a divalent, linear or branched $C_{1-10}$ hydrocarbon group optionally containing one or two ether bonds therein and 1 is a value of 3-300 and (ii) a radically polymerizable monomer comprising as a major component an acrylate monomer, a methacrylate monomer, or combinations thereof, wherein the weight ratio of (i) to (ii) in the copolymer ranges from 1:19-2:1;

(B) a low-viscosity silicone oil, (D) a low-boiling-point oil and combinations thereof;

(F) a cosmetic powder material.

8. A non-aqueous-makeup cosmetic composition comprising:

(A) 5.0-30% by weight of an acryl-silicone graft copolymer which is prepared by radically polymerizing (i) a dimethylpolysiloxane compound having the formula:

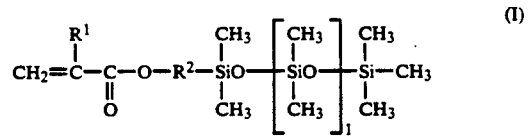

wherein $R^1$ is methyl or hydrogen, $R^2$ is a divalent, linear or branched $C_{1-10}$ hydrocarbon group optionally containing one or two ether bonds therein and 1 is a value of 3-300 and (ii) a radically polymerizable monomer comprising as a major component an acrylate monomer, a methacrylate monomer or combination thereof, wherein the weight ratio of (i) to (ii) in the copolymer ranges from 1:19-2:1;

(B) 2.5-30% by weight of a low-viscosity silicone oil;

(H) 20.0–80.0% by weight of a volatile hydrocarbon; and (F) 10.0–50% by weight of a cosmetic powder material.

9. A water-in-oil emulsion cosmetic composition comprising:

(A) 0.3–30% by weight of an acryl-silicone graft copolymer which is prepared by radically polymerizing (i) a dimethylpolysiloxane compound of the formula:

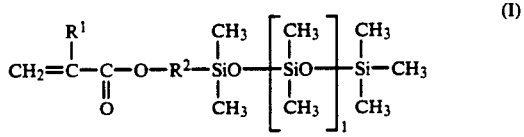

wherein $R^1$ is methyl or hydrogen, $R^2$ is a divalent, linear or branched $C_{1-10}$ hydrocarbon group optionally containing one or two ether bonds therein and 1 is a value of 3–300 and (ii) a radically polymerizable monomer comprising as a major component an acrylate monomer, a methacrylate monomer, or combinations thereof, wherein the weight ratio of (i) to (ii) in the copolymer ranges from 1:19–2:1;

(B) 15–57% by weight of a low-viscosity silicone oil or (D) at least one low-boiling-point oil in an amount such that the total amount of copolymer (A) and oil (D) ranges from 60–100% by weight in the oil component mixture, or combinations thereof; and (I) 0.1–10% by weight of a surface active agent; and (J) 5–69.9% by weight water, and wherein the total amount of (a) component (A) plus (b) component (B) or (D), or both, is 30–60% by weight.

* * * * *